US 8,165,372 B2

(12) United States Patent
Ishikawa et al.

(10) Patent No.: US 8,165,372 B2
(45) Date of Patent: Apr. 24, 2012

(54) INFORMATION PROCESSING APPARATUS FOR REGISTRATING MEDICAL IMAGES, INFORMATION PROCESSING METHOD AND PROGRAM

(75) Inventors: Ryo Ishikawa, Kawasaki (JP); Kiyohide Satoh, Kawasaki (JP); Shinji Uchiyama, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 187 days.

(21) Appl. No.: 12/755,276

(22) Filed: Apr. 6, 2010

(65) Prior Publication Data

US 2010/0239150 A1   Sep. 23, 2010

Related U.S. Application Data

(63) Continuation of application No. PCT/JP2009/004637, filed on Sep. 16, 2009.

(30) Foreign Application Priority Data

Dec. 5, 2008   (JP) .................................. 2008-311560

(51) Int. Cl.
G06K 9/00   (2006.01)
(52) U.S. Cl. ............................. 382/128; 128/922; 378/20
(58) Field of Classification Search ................. 382/100, 382/128, 129, 130, 131, 132; 378/4–27; 128/922; 600/407, 437, 451
See application file for complete search history.

(56) References Cited

U.S. PATENT DOCUMENTS

| | | | |
|---|---|---|---|
| 5,590,653 A * | 1/1997 | Aida et al. ..................... | 600/411 |
| 2003/0216648 A1 * | 11/2003 | Lizzi et al. .................... | 600/439 |
| 2005/0089205 A1 * | 4/2005 | Kapur et al. ................... | 382/128 |
| 2005/0251029 A1 * | 11/2005 | Khamene et al. .............. | 600/427 |
| 2007/0239004 A1 * | 10/2007 | Kakee et al. ................... | 600/437 |
| 2009/0005680 A1 * | 1/2009 | Jones et al. ..................... | 600/437 |
| 2009/0175518 A1 * | 7/2009 | Ikuma et al. ................... | 382/128 |
| 2010/0239150 A1 * | 9/2010 | Ishikawa et al. .............. | 382/131 |

FOREIGN PATENT DOCUMENTS

| | | |
|---|---|---|
| JP | 2004-016268 A | 1/2004 |
| JP | 3871747 B | 1/2007 |
| WO | 2006/068103 A | 1/2006 |
| WO | 2008/149573 A | 12/2008 |

OTHER PUBLICATIONS

Wein et al., "Automatic Registration and Fusion of Ultrasound with CT for Radiotherapy," Proc MICCAI 2005, vol. 2, pp. 303-311, 2005.
T.W. Sederberg, "Free-Form Deformation of Solid Geometric Models," Proc. SIGGRAPH '86, vol. 20, No. 4 pp. 151-160, 1986.
Fred L. Bookstein, "Principal Warps: Thin-Plate Splines and the Decomposition of Deformations," IEEE Transaction on Pattern Analysis and Machine Intelligence. vol. 11, No. 6, 1989.

* cited by examiner

*Primary Examiner* — Anand Bhatnagar
(74) *Attorney, Agent, or Firm* — Carter, DeLuca, Farrell & Schmidt LLP

(57) ABSTRACT

An information processing apparatus to register an ultrasonic image and a three-dimensional medical image at high speed is disclosed. The information processing apparatus includes: a medical image acquisition unit which acquires a medical image captured by a medical imaging apparatus in which an imaging unit captures an image of an object at a non-contact position with respect to the object, an ultrasonic image acquisition unit which acquires an ultrasonic image captured by an ultrasonic imaging apparatus in which an ultrasonic probe captures an image of the object at a position in contact with a surface of the object, and a coordinate transformation unit which transforms coordinates of the medical image or ultrasonic image with reference to the contact position on the ultrasonic image, so that image information of the medical image matches that of the ultrasonic image.

5 Claims, 17 Drawing Sheets

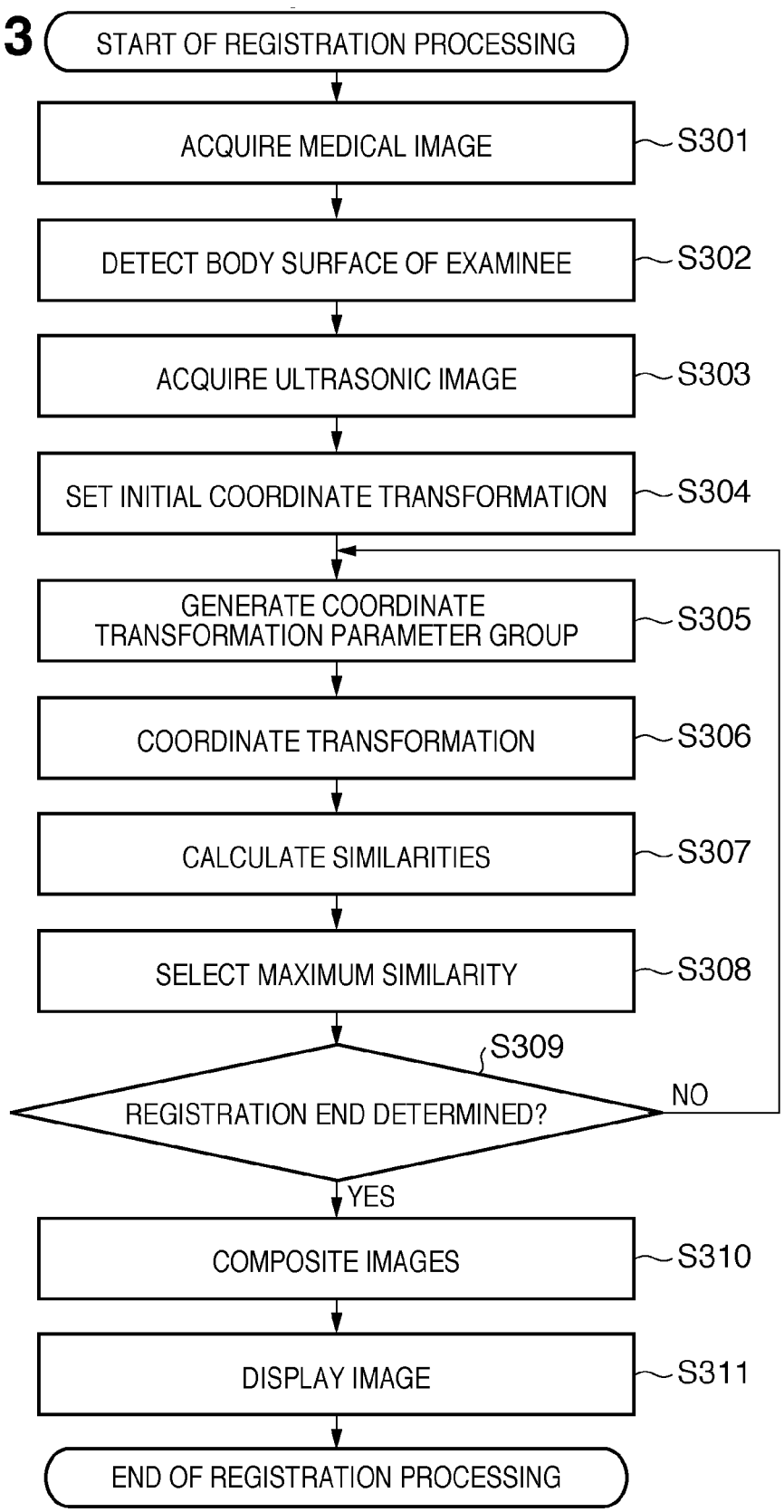

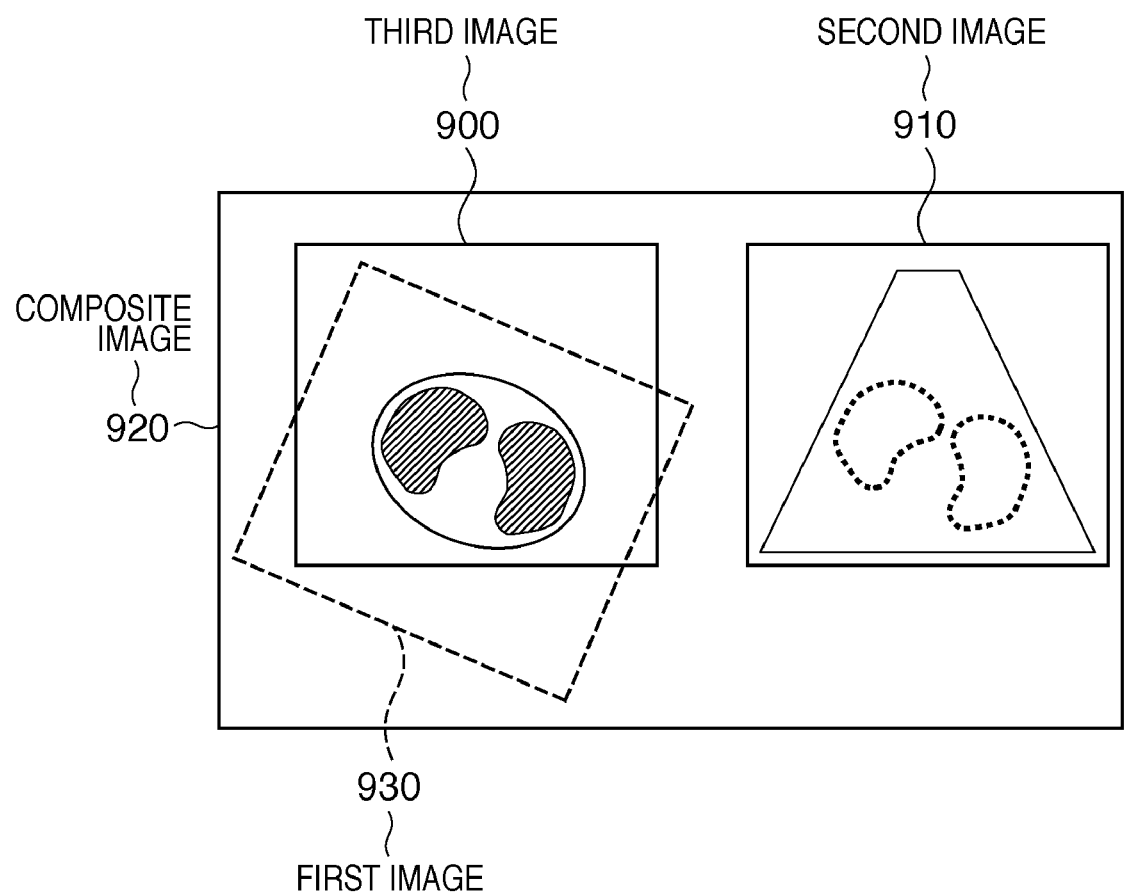

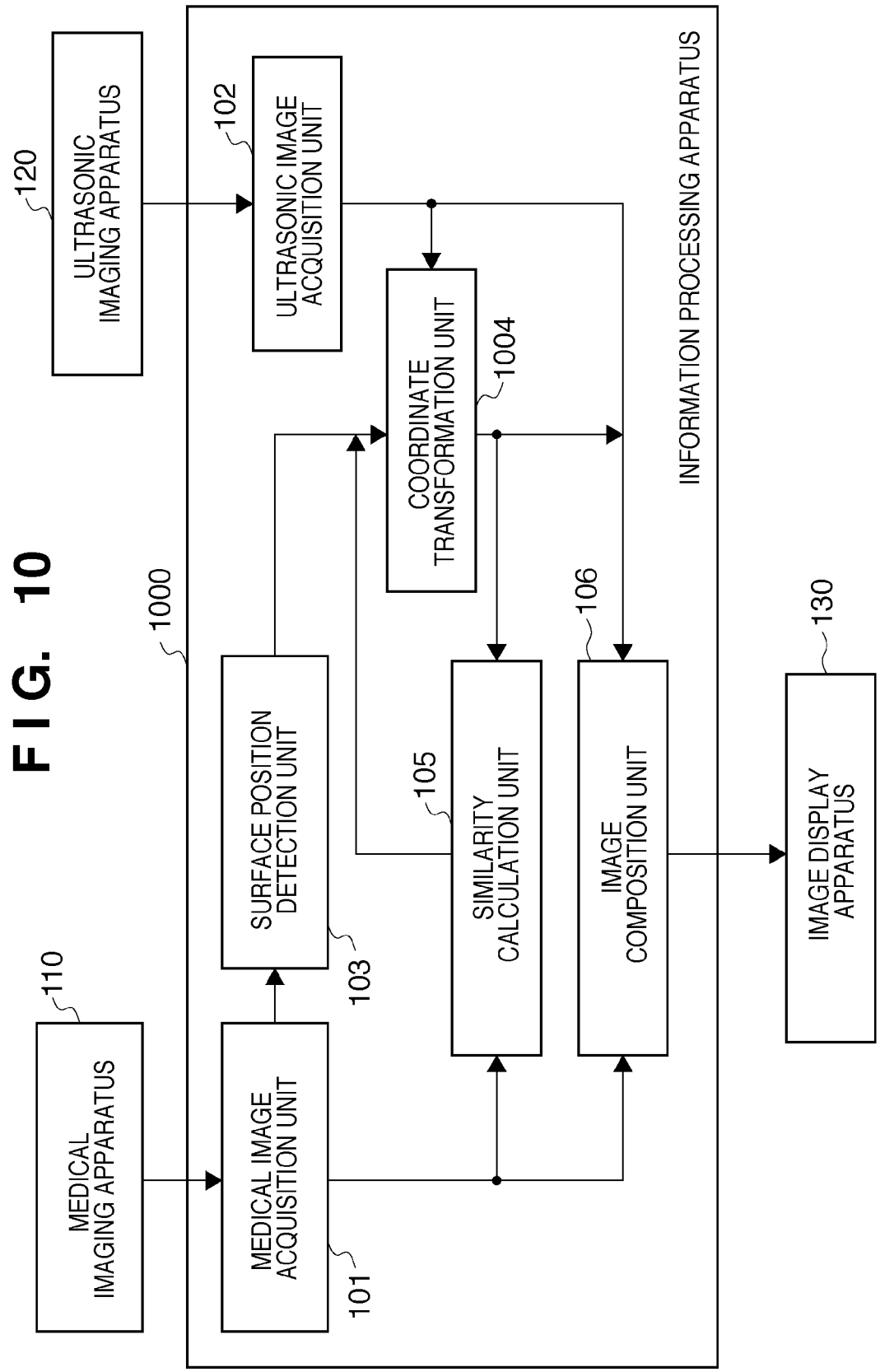

INFORMATION PROCESSING APPARATUS FOR REGISTRATING MEDICAL IMAGES, INFORMATION PROCESSING METHOD AND PROGRAM

CROSS REFERENCE TO RELATED APPLICATIONS

This application is a CONTINUATION of PCT application No. PCT/JP2009/004637 filed on Sep. 16, 2009 which claims priority from the benefit of Japanese Patent Application No. 2008-311560 filed on Dec. 5, 2008, the disclosures of which are hereby incorporated by reference herein in their entirety.

TECHNICAL FIELD

The present invention relates to an information processing technique required to register images obtained by capturing images of an object using a plurality of imaging units.

BACKGROUND ART

In recent years, a doctor displays a captured medical image on a monitor and interprets the medical image on the monitor to make a diagnosis (image diagnosis) of a state or temporal change of a morbid portion of a patient.

As an apparatus (medical imaging apparatus) for generating a medical image of this type, a plain radiographic apparatus, X-ray computed tomography apparatus (X-ray CT), nuclear magnetic resonance imaging apparatus (MRI), nuclear medicine diagnosis apparatus (SPECT, PET, etc.), ultrasonic imaging apparatus (US), and the like are available.

These medical imaging apparatuses respectively capture images of interior portions of human bodies using different imaging means, and respectively have different features.

For example, the plain radiographic apparatus irradiates a human body with X-rays, and records transmitted X-rays, thus capturing an image by obtaining a parallel projection image of X-ray absorption ratios of the interior portion of a human body. This plain radiographic apparatus has an advantage of acquiring information of the interior portion of a human body to have a relatively low dose within a relatively short period of time. On the other hand, since information of the radiation direction of X-rays is lost, detailed information of the interior portion of a human body cannot be obtained.

In case of the X-ray CT, a human body is irradiated with X-rays from various directions to obtain a large number of fluoroscopic images, and generates three-dimensional information of the interior portion of a human body by analyzing these fluoroscopic images. For this reason, the X-ray CT has an advantage of obtaining detailed information in the interior portion of a human body, although the dose and imaging time are increased compared to the plain radiographic apparatus.

Since the MRI can obtain three-dimensional information of the interior portion of a human body as in the X-ray CT, and is configured to image information using a magnetic resonance phenomenon, it can obtain physical information different from that of the X-ray CT which images the X-ray absorption ratios. On the other hand, at the time of imaging by the MRI, a contrast agent has to be normally applied to a human body, resulting in a heavy work load at the time of imaging.

The ultrasonic imaging apparatus (US) irradiates a human body with ultrasonic waves, and detects the ultrasonic waves reflected from the interior portion of the human body to acquire information of the interior portion of the human body. Then, by using a method called "B mode", three-dimensional information of the interior portion of the human body can be obtained. With this arrangement, unlike the X-ray CT and the like, there is no invasion such as exposure with respect to a human body, and real-time imaging can be attained. Hence, there is an advantage of making imaging and observation at the same time. On the other hand, an image (ultrasonic image) of the ultrasonic imaging apparatus has a high signal to noise ratio, which may often disturb diagnosis.

In image diagnosis which makes a diagnosis of a patient using medical images generated by the medical imaging apparatuses, an appropriate medical imaging apparatus is selected according to portions to be diagnosed and the types of diseases in consideration of the aforementioned different characteristics of the respective medical imaging apparatuses.

Furthermore, in order to realize more accurate image diagnosis, a plurality of medical images generated by a plurality of medical imaging apparatuses are used in some cases. For example, medical images of a single patient are captured using both the ultrasonic imaging apparatus (US) and MRI, and are combined to obtain more effective information in image diagnosis.

In order to combine a medical image (ultrasonic image) obtained from the ultrasonic imaging apparatus with a three-dimensional medical image obtained from a medical imaging apparatus other than the ultrasonic imaging apparatus, the ultrasonic image and three-dimensional medical image have to be registered.

However, in order to register the ultrasonic image and three-dimensional medical image, some problems have to be solved. First, the ultrasonic imaging apparatus normally captures an image while a document or operator holds an ultrasonic probe by the hand and freely moves it. For this reason, the capturing position of the captured ultrasonic image in a space with reference to a human body is not always revealed from only the ultrasonic image.

Second, the ultrasonic imaging apparatus normally captures a two-dimensional tomographic image of the interior portion of a human body, and the space dimension of information that can be acquired by imaging is different from that acquired by the X-ray CT, MRI, SPECT, PET, or the like, which generates a three-dimensional medical image.

As one approach to solve such problems, a method of measuring the position and orientation of the ultrasonic probe using an external sensor is available. More specifically, patent reference 1 discloses a technique in which a device for measuring the position and orientation is attached to the ultrasonic probe, a slice image corresponding to a portion captured by the ultrasonic imaging apparatus is acquired from a three-dimensional medical image captured in advance in accordance with the measurement value of the device, and two images are combined and displayed. According to this technique, an ultrasonic image as a two-dimensional tomogram and a three-dimensional medical image generated by another medical imaging apparatus can be observed in association with each other.

As another approach to solve the problems, it has been conventionally examined that an ultrasonic image and three-dimensional medical image are registered using image information included in the ultrasonic image and three-dimensional medical image. More specifically, non-patent reference 1 has proposed a method in which an ultrasonic simulation image generated based on a three-dimensional medical image acquired in advance and an ultrasonic image actually captured by the ultrasonic imaging apparatus are registered by associating them with each other based on image information.

PRIOR ART REFERENCES

Patent Reference

Patent Reference 1: Japanese Patent No. 3871747.

Non-Patent Reference

Non-patent Reference 1: W. Wein, B. Roper, and N. Navab, "Automatic registration and fusion of ultrasound with CT for radiotherapy," Proc. MICCAI 2005, vol. 2, pp. 303-311, 2005.

However, even when the position and orientation of the ultrasonic probe are measured using the external sensor like in patent reference 1, when the influence of, for example, the body movement of a patient is serious, it is difficult to attain precise registration.

For example, when the body position of a patient upon capturing a three-dimensional medical image is different from that of the patient upon capturing an ultrasonic image, since the body of the patient becomes deformed due to different influences of the gravity acting on the human body, it is difficult to attain precise registration.

In case of the ultrasonic imaging apparatus, since the ultrasonic probe is pressed against the body surface of a patient at the time of imaging, the body of the patient often becomes deformed by the pressure of the ultrasonic probe. In this case, it is difficult to precisely register an ultrasonic image and three-dimensional medical image.

By contrast, in case of non-patent reference 1, since the registration processing between an ultrasonic image and three-dimensional image is executed based on image information, even when the body of a patient becomes deformed, as described above, advanced registration can be attained by executing correction in consideration of such deformation.

However, since non-patent reference 1 requires a very large computation volume, registration cannot be done at high speed, thus impairing the synchronous effect between imaging and observation.

The present invention has been made in consideration of the aforementioned problems.

SUMMARY OF THE INVENTION

An information processing apparatus according to the present invention comprises the following arrangement. That is, an information processing apparatus comprises:

a first acquisition unit configured to acquire a first image captured by a first imaging unit in which an imaging unit that captures an image of a state of an interior portion of an object captures the image at a non-contact position with respect to the object;

a second acquisition unit configured to acquire a second image captured by a second imaging unit in which an imaging unit that captures an image of a state of an interior portion of the object captures the image at a position in contact with a body surface of the object; and a transformation unit configured to transform coordinates of one of the first image and the second image with reference to the contact position on the second image, so that image information of the first image matches image information of the second image.

According to the present invention, an ultrasonic image and three-dimensional medical image can be registered with high precision and at high speed.

Other features and advantages of the present invention will become apparent from the following description taken in conjunction with the accompanying drawings. Note that the same reference numerals denote the same or similar components throughout the accompanying drawings.

BRIEF DESCRIPTION OF DRAWINGS

The accompanying drawings, which are incorporated in and constitute a part of the specification, illustrate embodiments of the invention and, together with the description, serve to explain the principles of the invention.

FIG. 3 is a flowchart showing the sequence of registration processing in the information processing apparatus 100;

FIG. 9 is a view for explaining image composition processing;

FIG. 10 is a block diagram showing the functional arrangement of the information processing apparatus 1000 according to a modification of the first embodiment;

DETAILED DESCRIPTION OF THE EMBODIMENTS

Respective embodiments will be described in detail hereinafter with reference to the accompanying drawings as needed.

First Embodiment

1. Functional Arrangement of Information Processing Apparatus

Figure 1:
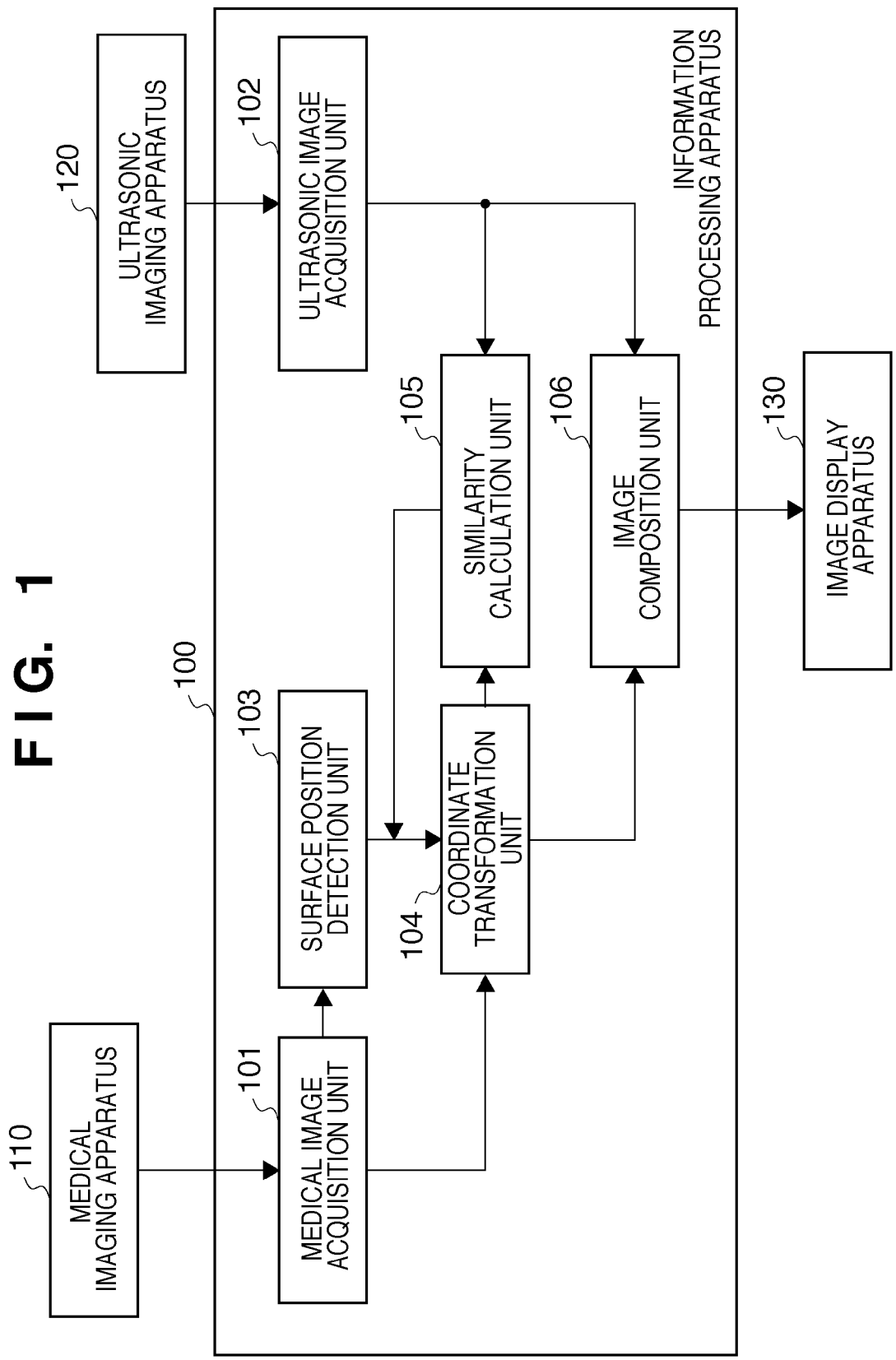
FIG. 1 is a block diagram showing the functional arrangement of an information processing apparatus 100 according to the first embodiment.

FIG. 1 is a block diagram showing the functional arrangement of an information processing apparatus 100 according to this embodiment. The information processing apparatus 100 is connected to a medical imaging apparatus 110 and ultrasonic imaging apparatus 120, and executes processing for registering images of a target region captured by the connected apparatuses. Note that the registration is to transform the coordinates of any of images so that pieces of image information in the images of the target region captured by the respective apparatuses match.

The medical imaging apparatus 110 is an apparatus such as an X-ray CT, MRI, SPECT, or PET, which captures a medical image of the interior portion of an examinee (object). The ultrasonic imaging apparatus 120 is an apparatus which captures an image of a second region of the interior portion of the examinee via ultrasonic waves by bringing an ultrasonic probe (imaging unit: not shown) into contact with the examinee.

A medical image acquisition unit 101 (a first acquisition unit) acquires a medical image (first image) of a first region of the examinee captured by the medical imaging apparatus 110.

An ultrasonic image acquisition unit 102 (a second acquisition unit) acquires an ultrasonic image (second image) captured by the ultrasonic imaging apparatus 120. A surface position detection unit 103 detects the position of a body surface (surface position) in the first region of the examinee by processing the first image, and generates that position information using position coordinates on a first coordinate system (a coordinate system defined on the first image).

A coordinate transformation unit 104 generates an image (third image) obtained by coordinate-transforming the first image onto a third coordinate system based on the position coordinates generated by the surface position detection unit 103 and an output value of a similarity calculation unit 105 (to be described below). The similarity calculation unit 105 calculates a similarity between the second and third images. An image composition unit 106 acquires the second and third images, and generates a composite image by compositing these images. An image display apparatus 130 displays the composite image acquired from the image composition unit 106 of the information processing apparatus 100.

2. Hardware Arrangement of Information Processing Apparatus

Figure 2:
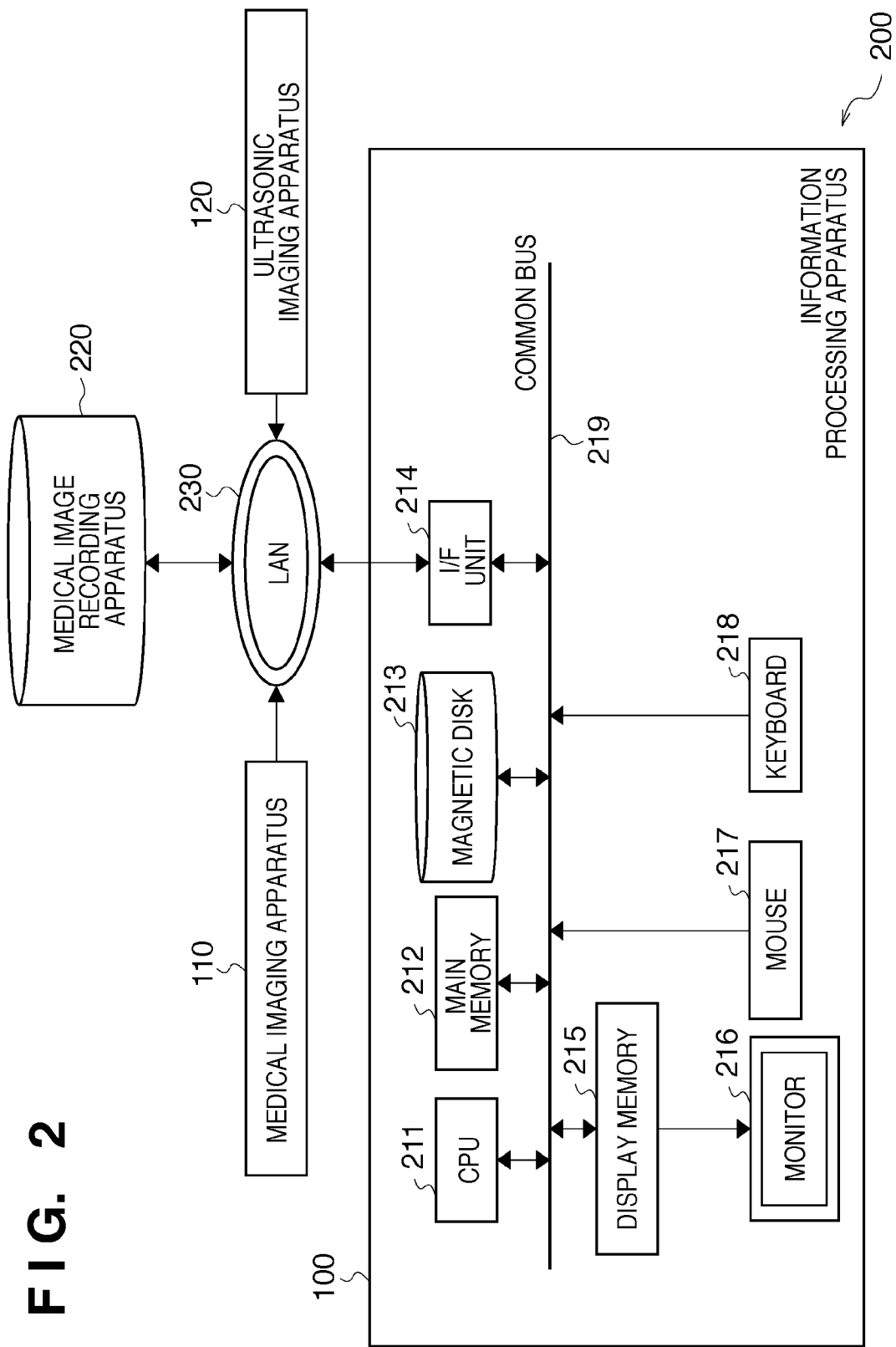
FIG. 2 is a block diagram showing the hardware arrangement of the information processing apparatus 100 according to the first embodiment, and the network arrangement of an information processing system 200 including the information processing apparatus.

FIG. 2 is a block diagram showing the hardware arrangement of the information processing apparatus 100 according to this embodiment and the network arrangement of an information processing system 200 including the information processing apparatus. As shown in FIG. 2, the information processing system 200 is configured by the information processing apparatus 100, the medical imaging apparatus 110, a medial image recording apparatus 220, a local area network (LAN) 230, and the ultrasonic imaging apparatus 120.

The information processing apparatus 100 can be implemented using, for example, a personal computer (PC). The information processing apparatus 100 includes a central processing unit (CPU) 211, main memory 212, magnetic disk 213, I/F unit 214, display memory 215, monitor 216, mouse 217, and keyboard 218.

The CPU 211 mainly controls the operations of respective components of the information processing apparatus 100. The main memory 212 stores a control program to be executed by the CPU 211, and provides a work area used when the CPU 211 executes the program.

The magnetic disk 213 stores various application software programs including an operating system (OS), device drivers of peripheral devices, and programs for implementing registration processing (to be described later) and the like. The display memory 215 temporarily stores display data for the monitor 216.

The monitor 216 includes, for example, a CRT monitor or liquid crystal monitor, and displays an image based on data from the display memory 215. The mouse 217 and keyboard 218 respectively allow the user to make pointing inputs and inputs of characters and the like. The respective components described above are connected via a common bus 219 to be able to communicate with each other.

In this embodiment, the information processing apparatus 100 can read out and acquire medical images and the like from the medical image recording apparatus 220 via the LAN 230. Alternatively, the information processing apparatus 100 may directly acquire medical images from the medical imaging apparatus 110 via the LAN 230.

However, the medical image acquisition mode of the present invention is not limited to them. For example, storage devices such as an FDD, CD-RW drive, MO drive, and ZIP drive may be connected to the information processing apparatus 100, and the information processing apparatus 100 may load and acquire medical images from these drives. Also, the processing results of this system may be saved in these storage devices.

The information processing apparatus 100 is connected to the ultrasonic imaging apparatus 120 via the LAN 230, and can acquire ultrasonic images captured by the ultrasonic imaging apparatus 120. The ultrasonic image acquisition mode is not limited to this, and the information processing apparatus 100 and ultrasonic imaging apparatus 120 may be directly connected to acquire ultrasonic images or the information processing apparatus 100 may load ultrasonic images from the aforementioned drives.

Furthermore, ultrasonic images captured by the ultrasonic imaging apparatus 120 may be recorded in the medial image recording apparatus 220, and the information processing apparatus 100 may acquire ultrasonic images read out from the medial image recording apparatus 220.

3. Sequence of Registration Processing

The registration processing between an ultrasonic image and three-dimensional medical image, which is executed in the information processing apparatus 100, will be described below.

An overview of the registration processing in the information processing apparatus 100 according to this embodiment will be described first. The information processing apparatus 100 according to this embodiment is characterized by executing a coordinate transformation of a three-dimensional medical image with reference to a contact position (body surface of an examinee) of the ultrasonic probe on an ultrasonic image upon execution of registration between the ultrasonic image and three-dimensional medical image.

Since the processing is executed with reference to the contact position of the ultrasonic probe in this way, even when the body of the examinee becomes deformed, precise registration can be attained. Since the processing is executed with reference to the contact position of the ultrasonic probe, a search space of coordinate transformation parameters required for registration can be limited, thus speeding up the registration processing.

Details of the registration processing in the information processing apparatus 100 will be described below with reference to the flowchart shown in FIG. 3.

<3.1 Step S301 (Medical Image Acquisition Processing)>

In step S301, the medical image acquisition unit 101 acquires a medical image generated when the medical imaging apparatus 110 (first imaging apparatus) captures an image of an examinee.

Note that the medical image may be acquired by directly inputting it from the medical imaging apparatus 110 to the information processing apparatus 100. Alternatively, medical images captured by the medical imaging apparatus 110 may be recorded in the medial image recording apparatus 220 shown in FIG. 2, and the medical image acquisition unit 101 may acquire a desired medical image read out from the medial image recording apparatus 220.

Information transfer between these apparatuses can be made via, for example, the LAN 230, as shown in FIG. 2, and an information transfer protocol in this case may use, for example, a DICOM format.

Note that the medical image gives arbitrary information associated with the examinee in a space whose position is defined on a certain coordinate system (first coordinate system). For example, in case of the X-ray CT, the medical image gives information associated with the magnitudes of X-ray absorption ratios at least at a plurality of positions. On the other hand, in case of the MRI, the medical image gives information associated with magnetic resonance strengths obtained by observing a nuclear magnetic resonance phenomenon.

This embodiment will exemplify a case in which the medical image is three-dimensional information (three-dimensional medical image). This information is described by $I_{3D}$ (x, y, z). Note that $I_{3D}(x, y, z)$ expresses a luminance value of a medical image at the position of coordinates (x, y, z) on a three-dimensional space in the form of a function. The acquired three-dimensional medical image $I_{3D}(x, y, z)$ is transmitted to the surface position detection unit 103 and the coordinate transformation unit 104.

<3.2 Step S302 (Body Surface Detection Processing of Examinee)>

In step S302, the surface position detection unit 103 detects the surface position of an object to be captured from the three-dimensional medical image $I_{3D}(x, y, z)$ acquired in step S301. This processing will be described below with reference to FIGS. 4A and 4B.

Figure 4A:
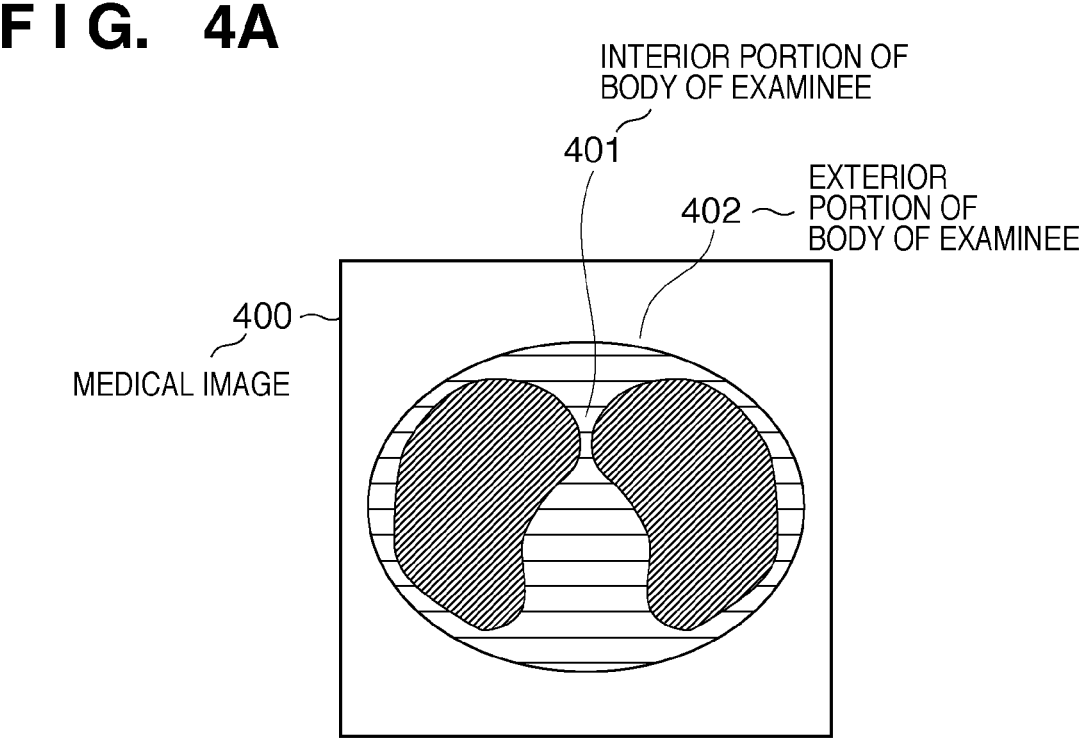
FIG. 4A is a view for explaining processing for detecting the position of a surface of an object to be captured from a three-dimensional medical image.

FIG. 4A is a view which expresses the three-dimensional medical image $I_{3D}(x, y, z)$ acquired in step S301 as a two-dimensional image for the descriptive convenience on the plane of paper.

The medical image shown in FIG. 4A is, for example, a sectional image of the abdomen of the examinee captured by, for example, the X-ray CT. As shown in FIG. 4A, the medical image visually includes a region of an interior portion 401 of the body of the examinee, and a region of an exterior portion 402 of the body of the examinee.

Figure 4B:
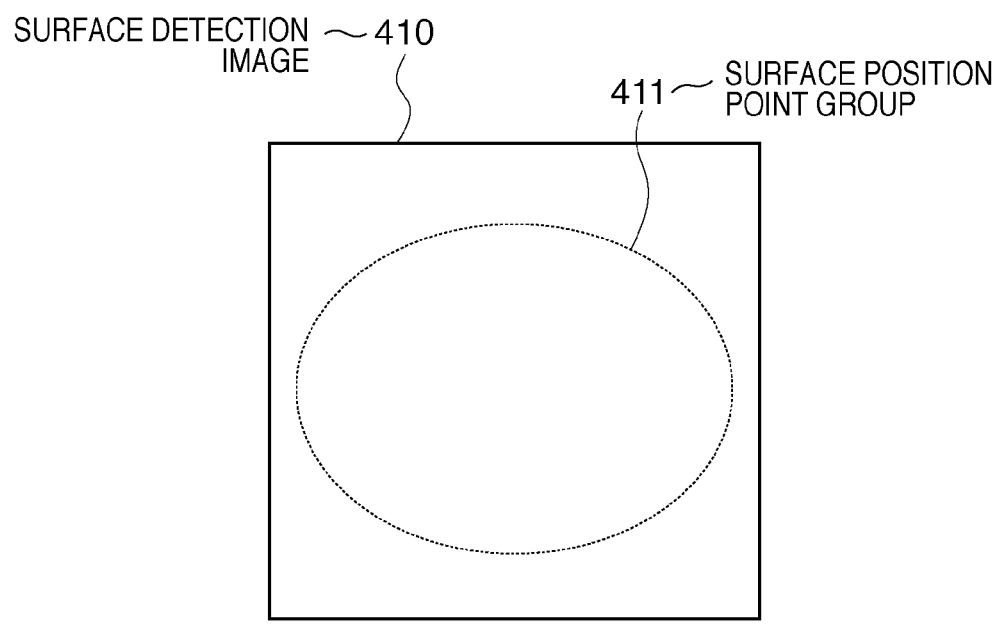
FIG. 4B is a view for explaining processing for detecting the position of a surface of an object to be captured from a three-dimensional medical image.

FIG. 4B shows a surface detection image 410 obtained by detecting the boundary between the interior portion 401 and exterior portion 402 of the body of the examinee from a medical image 400 shown in FIG. 4A. Various detection methods of the surface position are available. For example, a method of calculating the spatial gradient of luminance values of the medical image 400, and applying threshold processing to the magnitude of the spatial luminance gradient may be used.

As other methods, methods of detecting the edge of an image such as a Laplacian filter, Sobel filter, and Canny operator may be used. Alternatively, the surface of the examinee may be detected using a method of designating a partial region of the exterior portion (or interior portion) of the examinee, and growing that region when neighboring pixel values of the region satisfy a certain condition (region growing method). Alternatively, a method of detecting the surface by fitting an outline of the surface of the examinee using an implicit function (e.g., a level set method) may be used.

When noise components are mixed in the medical image, it is desired that after a smoothing filter such as a Gaussian filter or median filter is applied to reduce the noise components in the image, the aforementioned surface position detection method is executed.

The method of detecting the surface position from the medical image need not always be automatically executed by image processing. For example, the user may manually designate the surface position using, for example, the mouse 217 and keyboard 218 shown in FIG. 2.

Alternatively, from a plurality of pieces of surface position information automatically detected by, for example, image processing, surface position information to be used in subsequent processing may be selected based on a user's designation.

In this embodiment, assume that a point group 411 of N surface positions is detected from the medical image, as shown in FIG. 4B, and that point group is recorded as a position coordinate vector on the first coordinate system. In this embodiment, this vector is described by $x_{si}=(x_{si}, y_{si}, z_{si})^T$ for $1 \leq i \leq N$.

<3.3 Step S303 (Ultrasonic Image Acquisition Processing)>

In step S303, the ultrasonic image acquisition unit 102 acquires an ultrasonic image (second image) generated when the ultrasonic imaging apparatus 120 (second imaging apparatus) captures an image of the examinee.

Note that the ultrasonic image may be acquired by directly inputting it in synchronism with imaging of the ultrasonic imaging apparatus 120. Alternatively, the ultrasonic image may be acquired by reading it out from ultrasonic images which were previously captured by the ultrasonic imaging apparatus 120 and were recorded in the medial image recording apparatus 220 shown in FIG. 2.

Note that the ultrasonic image may be either a two-dimensional image or three-dimensional image, and may be any types of ultrasonic images such as a Doppler image and elastography. This embodiment will exemplify a case in which the ultrasonic image to be acquired is a two-dimensional B-mode tomographic image of the examinee.

Figure 5:
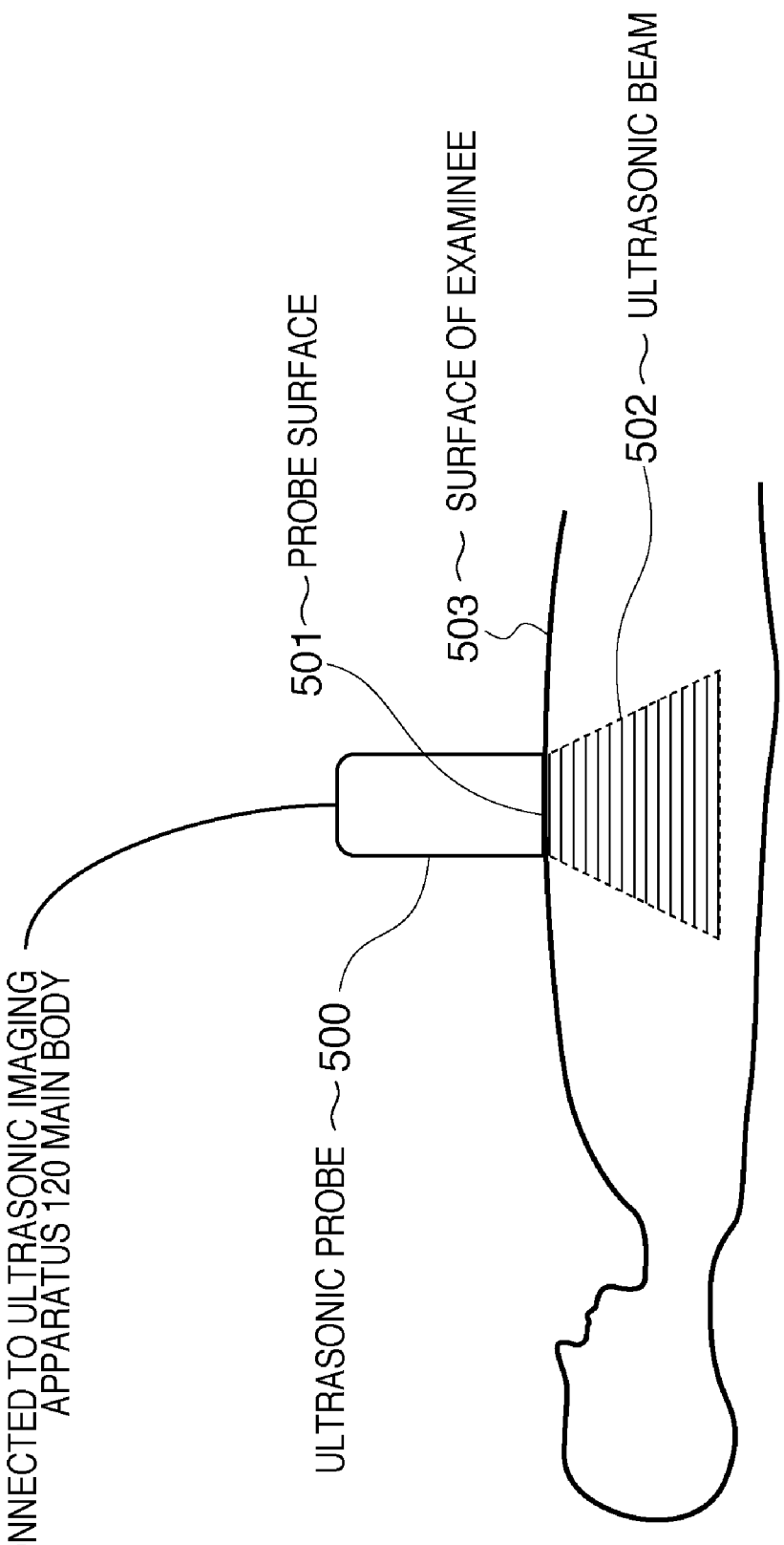
FIG. 5 is a view showing a state in which an ultrasonic imaging apparatus 120 captures an image of an examinee.

FIG. 5 is a view showing a state in which the ultrasonic imaging apparatus 120 shown in FIG. 1 captures an image of the examinee. In FIG. 5, an ultrasonic probe 500 emits an ultrasonic beam 502 from a probe surface 501 under the control of the ultrasonic imaging apparatus 120, and receives ultrasonic waves reflected by the interior portion of the examinee. At this time, the probe surface 501 is set to be in contact with a surface 503 of the examinee.

Figure 6:
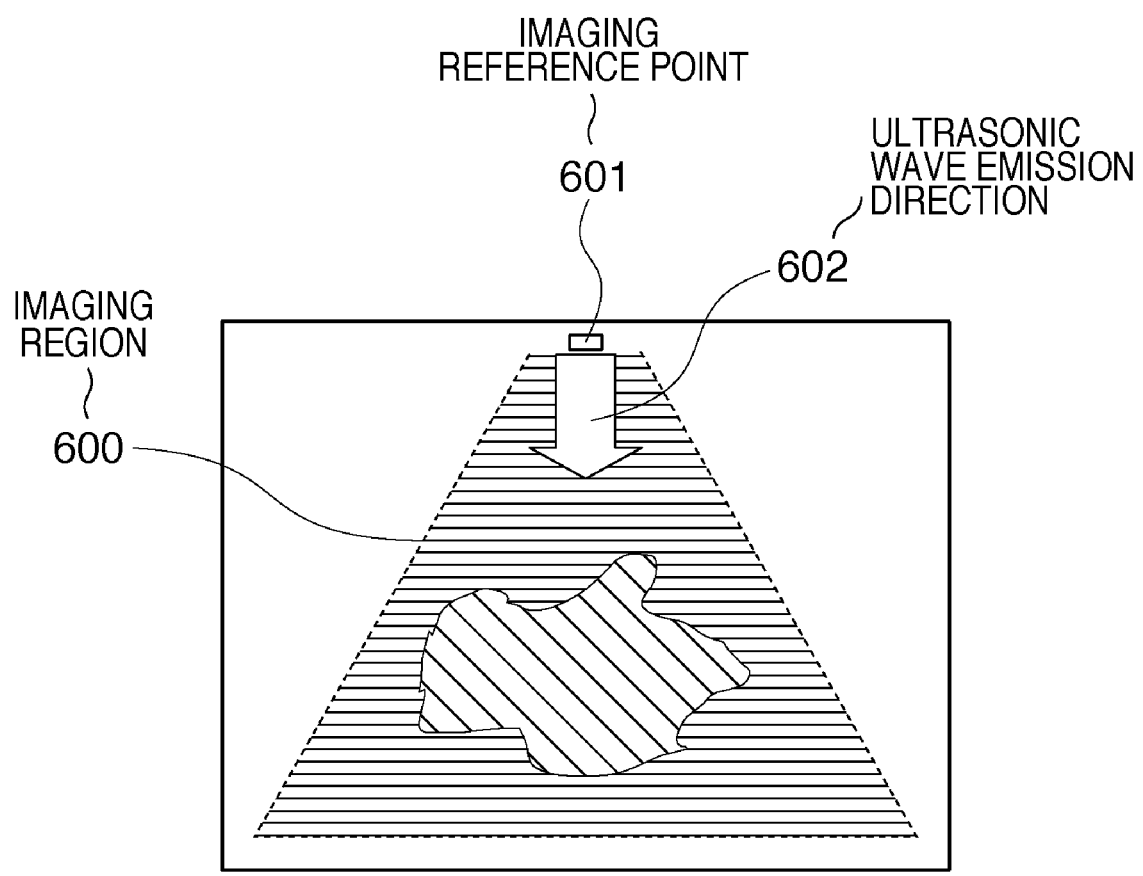
FIG. 6 is a view showing an example of an ultrasonic image captured by the ultrasonic imaging apparatus 120.

FIG. 6 is a view showing an example of an ultrasonic image captured by the ultrasonic imaging apparatus 120 shown in FIG. 1. As shown in FIG. 6, an imaging region 600 displays an ultrasonic image of the interior portion of the examinee obtained when the ultrasonic probe 500 in FIG. 5 emits the ultrasonic beam 502 and receives the reflected waves.

An imaging reference point 601 is a position on the ultrasonic image corresponding to the probe surface 501 in FIG. 5. As described above, the probe surface 501 is set to be in contact with the surface 503 of the examinee. For this reason, the imaging reference point 601 also corresponds to a contact between the probe surface 501 and the surface 503 of the examinee.

An ultrasonic wave emission direction 602 is a direction from the imaging reference point 601 toward the imaging region 600. In this embodiment, a coordinate system with reference to the coordinates of the imaging reference point on the ultrasonic image is defined, and is called a "second coordinate system". The imaging reference point 601 is defined by a position (coordinates) on the second coordinate system. The ultrasonic wave emission direction 602 is defined by a direction vector on the second coordinate system.

<3.4 Steps S304 to S309 (Processes Associated with Registration)>

The processes in steps S304 to S309 are those associated with registration between the medical image (first image) and ultrasonic image (second image).

In this embodiment, the first and second images are those obtained by capturing the identical examinee. However, the respective images are captured by the different apparatuses and have different reference coordinates. Therefore, images of a target portion of the examinee captured by the respective apparatuses appear at different positions on the respective images.

The registration processing in this embodiment is processing for calculating the positional relationship between a reference coordinate system (first coordinate system) of the first image and that (second coordinate system) of the second image. By calculating this relationship, for example, the correspondence between the position of a certain target portion on the first image and a position on the second image can be revealed.

Figure 7A:
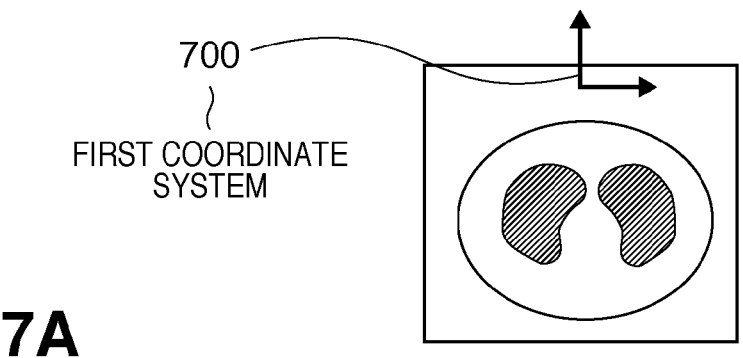
FIG. 7A is a view for explaining registration of images respectively captured on different coordinate systems.

FIGS. 7A to 7D are views for explaining registration of images captured on different coordinate systems. FIG. 7A shows an image obtained by capturing that of a target portion on a first coordinate system 700. Assume that this image is the medical image (first image) of this embodiment.

Figure 7B:
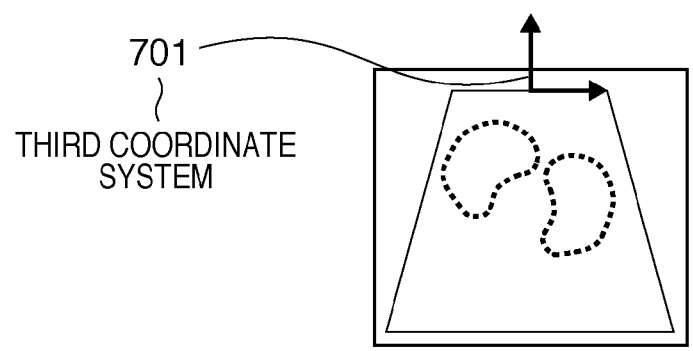
FIG. 7B is a view for explaining registration of images respectively captured on different coordinate systems.

FIG. 7B shows an image obtained by capturing that of the target portion on a second coordinate system 701 which is different from the first coordinate system 700. Assume that this image is the ultrasonic image (second image) of this embodiment. Note that this embodiment explains the medical image as a three-dimensional image, but FIG. 7B illustrates it as a two-dimensional image for the descriptive convenience on the plane of paper.

Figure 7C:
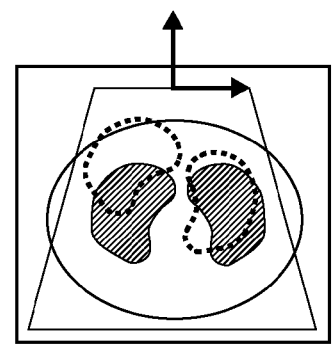
FIG. 7C is a view for explaining registration of images respectively captured on different coordinate systems.

FIG. 7C shows a composite image under the assumption that the first coordinate system 700 in FIG. 7A and the second coordinate system 701 in FIG. 7B match. However, in practice, since the first coordinate system 700 and second coordinate system 701 are different coordinate systems, the composite image in FIG. 7C is displayed to have deviated outlines of the target portion.

Figure 7D:
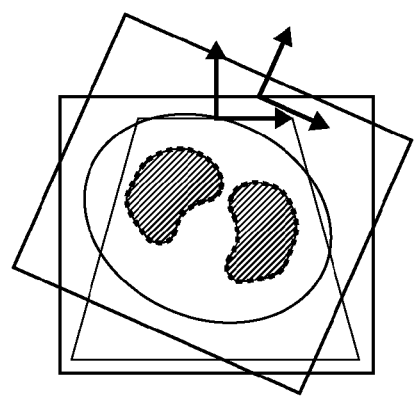
FIG. 7D is a view for explaining registration of images respectively captured on different coordinate systems.

On the other hand, FIG. 7D is a view showing a composite image of the two images by applying a transformation so as to correct the positional relationship between the first coordinate system 700 and second coordinate system 701. Originally, since these images are obtained by capturing the identical examinee, a composite image in which the identical target portions of the two images overlap each other can be generated by executing the correct coordinate system transformation.

The processes in steps S304 to S308 of this embodiment to be described below are those for correcting the positional relationship between images captured on different coordinate systems in this way (registration processing).

In the following description, assume that the medical image and ultrasonic image are obtained by capturing those of a target portion without any spatial distortion and twist, and the positional relationship between the two coordinate systems can be expressed by a rigid transformation.

In this case, the relationship between pixels $x_{3D}$ and $x_{US}$ indicating an identical portion on the medical image and ultrasonic image can be described by:

$$x_{US} R_{3D \to US} x_{3D} + t_{3D \to US} \quad \text{[Mathematical 1]}$$

where $R_{3D \to US}$ is an orthonormal 3×3 rotation matrix, and $t_{3D \to US}$ is a translation vector in respective axis directions. Each of the rotation matrix and translation vector in (Mathematical 1) has three degrees of freedom, and the characteristics of the rigid transformation can be expressed by a total of six parameters. Also, when a coordinate value is described as an extended vector $(x, y, z, 1)^T$, (Mathematical 1) can be rewritten as:

$$x_{US} = T_{3D \to US} x_{3D} \quad \text{[Mathematical 2]}$$

where $T_{3D \to US}$ is a 4×4 matrix given by:

$$T_{3D \to US} = \begin{pmatrix} R_{3D \to US} & t_{3D \to US} \\ 0 & 1 \end{pmatrix} \quad \text{[Mathematical 3]}$$

The registration processing in this embodiment is executed under a constraint condition that any of the N surface positions on the first coordinate system of the examinee calculated in step S302 matches (is defined with reference to) the imaging reference point 601 on the second coordinate system shown in FIG. 6. That is, matching between information associated with the shape of the surface of the examinee on the first image and that associated with the position and/or orientation of the ultrasonic probe on the second image is used as the constraint condition. This is a constraint condition derived from the imaging principle of the ultrasonic imaging apparatus which performs imaging while the imaging reference point 601 as an ultrasonic wave receiving unit is in contact with the surface of the examinee.

In this embodiment, under the aforementioned constraint condition, parameters of the coordinate transformation $T_{3D \to US}$ of the two coordinate systems, which can increase a similarity between the first and second images, are estimated by iterative calculations.

In order to estimate the coordinate transformation parameters, in this embodiment, an initial coordinate transformation (initial values of estimated values of the coordinate transformation parameters) $T_{init}$ is set in step S304. Then, a candidate group of the coordinate transformation parameters is generated based on this initial coordinate transformation in step S305.

Furthermore, third images (third image group) obtained when the coordinate transformations are applied to the first image using the respective candidates of the coordinate transformation parameters are generated in step S306. In step S307, similarities between the second image and the third images (third image group) generated using the candidates of the coordinate transformation parameters are evaluated.

Moreover, the candidate of the coordinate transformation parameters, which yield a maximum similarity, is selected as estimated values of the coordinate transformation parameters at the current timing in step S308. Then, the processes in steps S305 to S308 are repetitively executed unit it is determined in step S309 that a similarity satisfies a condition (for example, a similarity is equal to or larger than a certain threshold).

In this manner, the coordinate transformation parameters from the first coordinate system to the third coordinate system, which are required to obtain a third image with a high similarity with the second image, can be calculated. As a result, the coordinate transformation parameters which are approximate to (or match) a true value $T_{3D \to US}$ between the first coordinate system and second coordinate system can be calculated.

Details of the respective processes in steps S304 to S309 will be described below.

<3.4.1 Step S304 (Initial Coordinate Transformation Setting Processing)>

In step S304, the coordinate transformation unit 104 sets an initial coordinate transformation $T_{init}$ of coordinate transformation parameters. In this embodiment, a three-dimensional rigid transformation is assumed as an example of the coordinate transformation. For this reason, a total of six coordinate transformation parameters, that is, three parameters $(rx, ry, rz)_T$ of a rotation matrix $R_{init}$, and three parameters $(tx, ty, tz)^T$ of a translation vector $t_{init}$, are to be set.

Figure 8A:
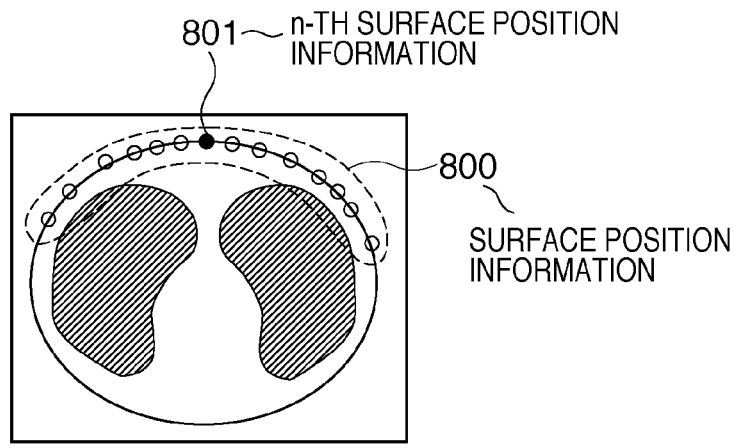
FIG. 8A is a view for explaining initial coordinate transformation setting processing.

As a method of setting the initial coordinate transformation, as shown in FIG. 8A, arbitrary n-th surface position information 801 is selected from N pieces of surface position information 800 having coordinate values $x_{si}(x_{si}, y_{si}, z_{si})^T$ (for $1 \leq i \leq N$).

In this case, assuming that the selected surface position information is $x_{sn}(x_{sn}, y_{sn}, z_{sn})^T$ on the first coordinate system, and the imaging reference point 601 is $x_p(x_p, y_p, z_p)^T$ on the second coordinate system, the translation vector $t_{init}$ is given by:

$$t_{init} = x_p - R_{init} x_n \qquad \text{[Mathematical 4]}$$

Note that a unit matrix can be set as the rotation matrix $R_{init}$. In addition, two or more pieces of surface position information having close distances to the selected n-th surface position information are further selected, and the rotation matrix can also be set based on these pieces of surface position information.

Figure 8B:
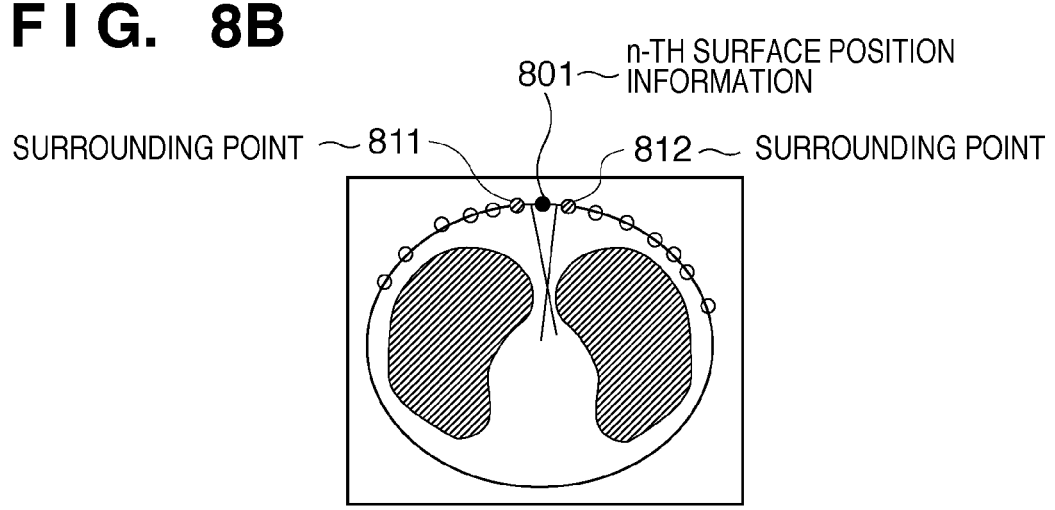
FIG. 8B is a view for explaining initial coordinate transformation setting processing.
Figure 8C:
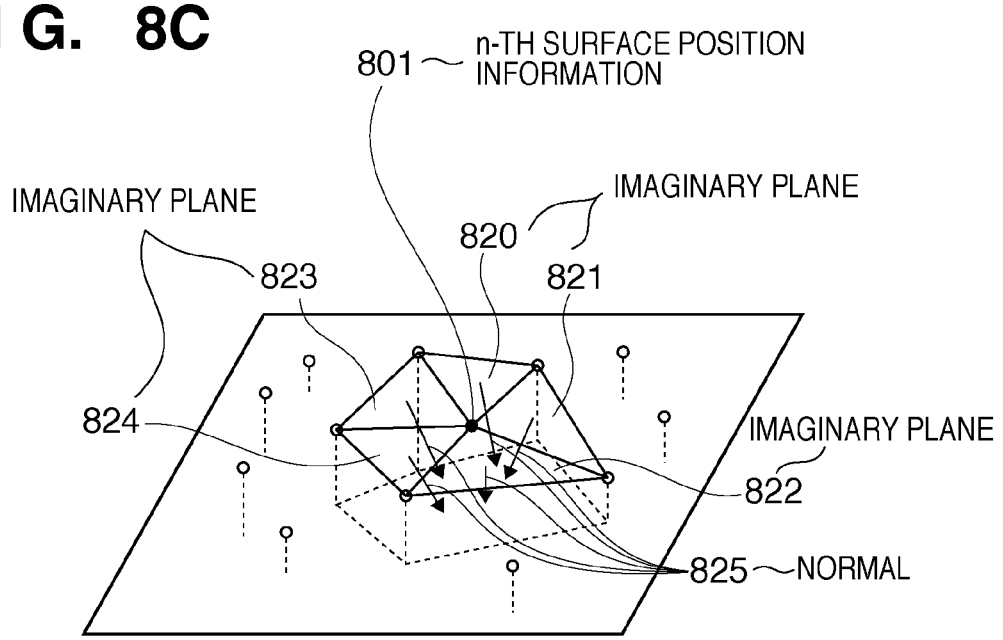
FIG. 8C is a view for explaining initial coordinate transformation setting processing.

In this case, more specifically, the rotation matrix can be set in the following sequence. As shown in FIG. 8B, the n-th surface position information 801 and its surrounding points 811 and 812 are selected from the plurality of pieces of surface position information. Since the first coordinate system is a three-dimensional coordinate system in practice, a plane 824 is generated from an imaginary plane 820 on the first coordinate system, as shown in FIG. 8C.

Then, the rotation matrix is set so that a normal 825 to that plane matches the ultrasonic wave emission direction 602 on the second coordinate system shown in FIG. 6. At this time, a degree of freedom is left in a rotation about the ultrasonic wave emission direction 602, and a setting of that component becomes indefinite. However, this value can be determined by an arbitrary method. For example, the value may be set in association with the body axis direction of the examinee that appears in the medical image, or a user's manual setting may be input.

<3.4.2 Step S305 (Coordinate Transformation Parameter Group Generation Processing)>

In step S305, the estimated values (six coordinate transformation parameters) of the coordinate transformation parameters at the current timing are respectively added with small changes to generate a new candidate of coordinate transformation parameters. As the candidate of the coordinate transformation parameters, a plurality of candidates (a candidate group of the coordinate transformation parameters) are generated by setting difference values as the small change values. In association with each candidate of the generated candidate group of the coordinate transformation parameters, a surface position of the examinee which is spatially close to the imaging reference point is selected, as given by:

$$x_{near} = \underset{x_{si}}{\operatorname{argmin}} \|Tx_{si} - x_p\| \ \{1 \leq i \leq N\} \qquad \text{[Mathematical 5]}$$

Then, the coordinate transformation parameters are corrected according to a deviation between these positions, as given by:

$$T' = \begin{pmatrix} I & x_p - Tx_{near} \\ 0 & 1 \end{pmatrix} T \qquad \text{[Mathematical 6]}$$

where $x_{si}$ represents the i-th position coordinates of the surface position information of the examinee on the first coordinate system, $x_p$ represents the position coordinates of the imaging reference point on the second coordinate system, T is a coordinate transformation matrix before correction, T' is a coordinate transformation matrix after correction, and I is a unit matrix.

According to this processing, the search range can be limited to coordinate transformation parameters which satisfy the constraint condition that the imaging reference point matches the surface position of the examinee.

<3.4.3 Step S306 (Coordinate Transformation Processing)>

In step S306, the coordinate transformation unit 104 executes coordinate transformations of the first image captured on the first coordinate system using respective coordinate transformation candidates based on the coordinate transformation candidate group calculated in step S305. Then, the coordinate transformation unit 104 generates a third image group on a third coordinate system group. More specifically, the coordinate transformation unit 104 applies the coordinate transformation processing described by:

$$I'(Tx_j) = I(x_j), \forall x_j \in \Omega \qquad \text{[Mathematical 7]}$$

where I is the first image, I' is the third image, T is the coordinate transformation matrix set in step S304 or S308, $x_j$ represents the image coordinates on the first coordinate system, and $\Omega$ is a set of all or some of image coordinates of the first image. As another method, this processing can be that described by:

$$I'(x_k') = I(T^{-1}x_k'), \forall x_k' \in \Omega' \qquad \text{[Mathematical 8]}$$

where $x_k'$ represents the image coordinates on the third coordinate system, and $\Omega'$ is a set of all or some of image coordinates of the third image. In step S305, a third image group corresponding to the coordinate transformation candidate group generated in step S304 is obtained by one of the above methods or another method.

<3.4.4 Step S307 (Similarity Calculation Processing)>

In step S307, the similarity calculation unit 105 executes matching between the third image group generated in step S306 and the second image acquired in step S303 to calculate similarities. Note that the similarity means a degree that two images are similar to each other, and can be calculated based on average square error criteria of pixel values, for example, as given by:

[Mathematical 9]
$$C_{SSD}(I'_{3D}, I_{US}) = -\frac{1}{M} \sum_{x_i \in \Omega_{I'_{3D}, I_{US}}} (I'_{3D}(x_i) - I_{US}(x_i))^2$$

where $I_{3D'}$ is the medical image, and $I_{US}$ is the ultrasonic image. Also, $\Omega_{I3D', IUS}$ represents a set of image coordinates of an overlapping region of $I_{3D'}$ and $I_{US}$. M is the number of elements of the image coordinate set $\Omega_{I3D', IUS}$, that is, the number of pixels of the overlapping image region. According to (Mathematical 9), the square error of the luminance values of the second image and third image can be calculated, thereby calculating a similarity between the second image and third image.

In place of the above similarity calculation method, a similarity can also be calculated using absolute value error criteria of luminance values, as given by:

[Mathematical 10]
$$C_{SAD}(I'_{3D}, I_{US}) = -\frac{1}{M} \sum_{x_i \in \Omega_{I'_{3D}, I_{US}}} |I'_{3D}(x_i) - I_{US}(x_i)|$$

In place of the above similarity calculation methods, a similarity can also be calculated using cross-correlation criteria of luminance values, as given by:

[Mathematical 11]
$$C_{CC}(I'_{3D}, I_{US}) = \frac{\sum_{x_i \in \Omega_{I'_{3D}, I_{US}}} (I'_{3D}(x_i) - I'_{3D\_ave})^2 \cdot (I_{US}(x_i) - I_{US\_ave})^2}{\sqrt{\sum_{x_i \in \Omega_{I'_{3D}, I_{US}}} (I'_{3D}(x_i) - I'_{3D\_ave})^2 \cdot \sum_{x_i \in \Omega_{I'_{3D}, I_{US}}} (I_{US}(x_i) - I_{US\_ave})^2}}$$

where $I_{3D\_ave'}$ and $I_{US\_ave}$ are respectively an average luminance value of the third image, and that of the second image.

In place of the above similarity calculation methods, a similarity can also be calculated using mutual information content criteria of luminance values, as given by:

$$C_{MI}(I_{3D}', I_{US}) = H(I_{3D}') + H(I_{US}) - H(I_{3D}', I_{US})$$ [Mathematical 12]

where H is a function which gives an entropy of a pixel value, and can be calculated by:

[Mathematical 13]
$$H(I) = -\sum_a p_I(a) \log p_I(a)$$

where $p_I(a)$ is a probability density function associated with the luminance values of an image I. In this embodiment that handles discrete luminance values, more specifically, this probability density function can be directly obtained by generating a histogram of the luminance values in the image I.

According to this method, even when images which are to undergo similarity evaluation have different luminance characteristics, a similarity with a relatively high accuracy which reflects, for example, a degree of matching of structures included in the images can be evaluated.

In place of the above similarity calculations, a similarity can also be calculated using normalized mutual information content criteria of luminance values, as given by:

[Mathematical 14]
$$C_{NMI}(I'_{3D}, I_{US}) = \frac{H(I'_{3D}) + H(I_{US})}{H(I'_{3D}, I_{US})}$$

According to this method, similarity evaluation which eliminates the influence due to different sizes of overlapping regions between images which are to undergo similarity evaluation can be attained.

In addition, various other methods of extracting image features such as the luminance value gradient and edges from images, and evaluating a similarity using the extraction results are available. The similarity calculation according to the present invention can use any of the aforementioned criteria or other criteria similar to them. The aforementioned criteria may be solely used, or may be used in combination by calculating their weighted sum.

<3.4.5 Step S308 (Maximum Similarity Selection Processing)>

In step S308, the similarity calculation unit 105 selects a coordinate transformation candidate which assumes a maximum similarity based on the similarity values associated with the plurality of coordinate transformation candidates calculated in step S307.

<3.4.6 Step S309 (Registration end Determination Processing)>

The coordinate transformation unit 104 determines in step S309 if the processes associated with registration in steps S305 to S308 are to end or are further repetitively executed. In this determination process, when the similarity obtained in step S308 is larger than a preset threshold, it is determined that the processes are to end; otherwise, it is determined that the process returns to step S305 to repeat the registration processes.

In addition, in the iterative calculations in steps S305 to S308, when an increment of the similarity obtained in step S308 becomes equal to or smaller than a preset threshold, it may be determined that the processes are to end. According to these methods, an effect of appropriately ending the processing without any excessive repetitive processes when the similarity which satisfies the set condition is obtained can be provided.

In addition to the aforementioned end determination methods, for example, the number of times of the repetitive processes is counted, and when the count value exceeds a preset value, the repetitive processes may be ended. According to this method, an effect of assuring the real-time performance of the whole system since a series of iterative calculations can be ended within a predetermined period of time can be provided.

<3.4.7 Step S310 (Image Composition Processing)>

In step S310, the image composition unit 106 composites the third image obtained by the processes in steps S304 to S309 and the second image acquired in step S303. Various image composition methods are available, and the present invention is not particularly limited to a specific image composition method.

For example, as shown in FIG. 9, a composite image 920 can be generated by juxtaposing a third image 900 and second image 910. Note that the third image 900 is an image generated based on the coordinate transformation, which is calculated in the processes in steps S304 to S309, of the medical image (first image).

In addition, the second image 910 and third image 900 may be displayed while superimposing them at an identical position. At this time, the second and third images may be superimposed by converting them to have different colors, different luminance levels, or different patterns. As a result, an effect of allowing easier comparison and discrimination of the two images can be provided.

Note that the image composition method is not limited to the above method. For example, an image may be generated by volume-rendering the third image 900, and a composite image may be generated by overlying the second image on that image. According to this method, an effect of generating a composite image which simultaneously expresses comprehensive information of the third image and the position and orientation relationship between the second and third image can be provided.

The number of composite images is not limited to one. For example, a mechanism which alternately displays the second and third images in response to, for example, a user operation may be provided. Alternatively, composite images may be generated to be observed from different viewpoints by, for example, a user operation while maintaining the positional relationship between the second and third images. Also, the aforementioned composite image generation processing is executed a plurality of times, and an image may be generated by further compositing images obtained by the respective composition processes.

<3.4.8 Step S311 (Image Display Processing)>

In step S311, the image display apparatus 130 displays the composite image generated by the image composition unit 106 of the information processing apparatus 100. The image display apparatus 130 may use a medical monitor for interpretation, or a monitor attached to the ultrasonic imaging apparatus 120 may be used as the image display apparatus.

Not only the composite image is displayed on the image display apparatus 130, but also it may be recorded in the medical image recording apparatus 220 shown in FIG. 2 or may be printed on, for example, a paper medium without being displayed.

As can be seen from the above description, this embodiment focuses attention on the fact that the imaging reference point of the ultrasonic probe is in contact with the body surface of the examinee upon imaging using the ultrasonic imaging apparatus. Using this fact as the constraint condition, the search space of the coordinate transformation parameters required for registration is limited.

As a result, with the information processing apparatus 100 according to this embodiment, the medical image and ultrasonic image can be registered with high precision and at high speed.

4. Modification 1 of this Embodiment

The aforementioned embodiment has explained the case in which one of pieces of surface shape information of the examinee is selected, an initial coordinate transformation set based on the selected information is repetitively calculated. However, the present invention is not limited to this. For example, in step S304 the coordinate transformation unit 104 may select all or some of a plurality of pieces of surface shape information of the examinee, and may set a plurality of initial coordinate transformations.

As a simpler method, the plurality of initial coordinate transformations set in step S304 may be directly used as a coordinate transformation candidate group, that is, the processes in step S306 and subsequent steps may be executed without executing the process in step S305.

According to these methods, an effect of enhancing the probability of avoiding convergence to a local solution caused by the setting of the initial coordinate transformation can be provided.

As a still simpler method, the determination process in step S309 may be skipped, and the process in step S310 may be executed based on the processing result in step S308 that calculates the coordinate transformation parameters which can yield a maximum similarity from the candidate group of the coordinate transformation parameters.

According to this method, an effect of shortening the processing time of the registration processing can be further provided in addition to the aforementioned effect.

5. Modification 2 of this Embodiment

The aforementioned embodiment has explained the case in which one medical image (first image) and ultrasonic image (second image) are registered. However, the present invention is not limited to this, and the registration may be executed in the following sequence.

More specifically, two medical images (first and fourth images) are captured in advance, and coordinate transformation (first transformation) parameters between these images are calculated in advance. Then, coordinate transformation (second transformation) parameters are calculated for the first image and an ultrasonic image (second image) by the method described in the above embodiment. Then, the second transformation is further applied to the first transformation to calculate coordinate transformation (third transformation) parameters between the fourth and second images.

With this processing, mutual coordinate transformation parameters among the first, second, and fourth images can be obtained, and observation is allowed by associating these images. According to this method, for example, an effect of allowing to register the ultrasonic image and medical image even when the fourth image does not include the surface of the examinee or it is difficult to detect the surface position of the examinee can be provided.

6. Modification 3 of this Embodiment

The aforementioned embodiment has explained the case in which one medical image (first image) and one ultrasonic image (second image) are registered. However, the present invention is not limited to this. For example, the second image may include a plurality of time-series ultrasonic images, and the registration processing may be successively executed for this image sequence.

In this case, the registration processing is applied to an immediately preceding captured ultrasonic image in a time-series or that captured before that timing, and is then applied to the next image using the result of the former processing. For example, the result of the previous registration processing may be used as an initial value of the next registration processing.

According to this method, an effect of reducing the number of times of repetitive processes since the processing can be started from an initial value close to the true value of the registration when imaging positions of a successive ultrasonic image sequence are close to each other can be expected.

This processing need not be executed in ascending order of imaging time. For example, ultrasonic images in a time-series may be accumulated and the aforementioned processing may be executed in an order opposite to the imaging order. Also, the processing may be executed in both ascending and descending orders of imaging, and the respective results may be compared. According to this method, an effect of assuring stable registration processing and detecting failures can be provided.

7. Modification 4 of this Embodiment

The aforementioned embodiment has explained the case in which the third image is generated by coordinate-transforming the medical image (first image), and the registration is executed using a similarity between the third image and ultrasonic image (second image). However, the present invention is not limited to this.

For example, as shown in FIG. 10, an image obtained by coordinate-transforming the ultrasonic image (second image) may be used as the third image, and the registration may be executed to increase a similarity between the first and third images. In this case, in step S306 a coordinate transformation unit 1004 executes a coordinate transformation of the ultrasonic image (second image) using respective coordinate transformation parameter candidates calculated in step S305.

As a result, when the data size of the ultrasonic image (second image) is smaller than that of the medical image (first image), the two images can be registered with a smaller computation volume.

8. Modification 5 of this Embodiment

The aforementioned embodiment has explained the case in which the registration is executed under the constraint condition that the position of the imaging reference point 601 matches a certain position of the surface 503 of the examinee. However, the present invention is not limited to this as long as the positional relationship which is established between information associated with the surface shape of the examinee on the first image and information associated with the position and/or orientation of the ultrasonic probe on the second image is used.

For example, the registration may be executed using an evaluation function which includes a term that makes the imaging reference point of the probe on the second image close to the surface position of the examinee on the first image.

More specifically, the registration can be implemented by subtracting or taking off, from a similarity calculated in step S306, a distance between the imaging reference point 601 and the position of the surface 503 of the examinee as a penalty, as given by:

$$C' = C - \alpha \|Tx_{near} - x_p\|$$ [Mathematical 15]

where C is a similarity which is calculated in step S306 and does not consider any penalty, C' is a similarity which considers the penalty, and α is a constant which decides a weight of the penalty.

Note that this modification has explained the case in which the distance between the imaging reference point 601 and the position of the surface 503 of the examinee is used as a penalty. However, the present invention is not limited to this. For example, a deviation between the ultrasonic wave emission direction 602 and a normal direction to each position of the surface 503 of the examinee may be used as a penalty. Alternatively, a new penalty may be calculated by combining that based on the distance between the imaging reference point 601 and the position of the surface 503 of the examinee, and that based on the deviation between the ultrasonic wave emission direction and normal direction, and a calculation similar to (Mathematical 15) may be made.

As a result, the constraint condition that the imaging reference point matches the surface position of the examinee can be relaxed, thus allowing more flexible registration.

9. Modification 6 of this Embodiment

The aforementioned embodiment has explained the case in which the surface position of the examinee is calculated as a point group. However, the present invention is not limited to this. For example, image processing may be applied to the medical image (first image) to estimate the surface of the examinee, and the coordinate transformation parameter settings in step S304 and (or) step S305 may be changed based on that result.

More specifically, the calculation of the penalty based on the distance between the imaging reference point and surface position described in Modification 5 above may be made in consideration of the above estimated degree of surface.

With this arrangement, even when it is difficult to detect the precise surface position of the examinee from the medical image (first image), appropriate registration processing can be executed according to the estimation value of the surface.

10. Modification 7 of this Embodiment

The aforementioned embodiment has explained the case in which the ultrasonic image (second image) is a two-dimensional tomographic image. However, the present invention is not limited to this. For example, the ultrasonic image may be a three-dimensional image captured by the ultrasonic imaging apparatus 120. In this case, since the information volume of the second image becomes large, more precise registration is allowed, thus presenting a more effective composite image in image diagnosis.

11. Modification 8 of this Embodiment

The aforementioned embodiment has explained the case in which the second image is an ultrasonic image. However, the present invention is not limited to this, and may use any other captured images as long as they are captured by imaging methods which are subject to arbitrary constraints from the surface position of an object to be captured upon imaging the interior portion of the object to be captured.

For example, the second image may be a PAT (Photo Acoustic Tomography) image generated based on an acoustic signal which is generated from the interior portion of the object to be captured by irradiating the object to be captured with a laser beam, and is received by a probe.

12. Modification 9 of this Embodiment

The aforementioned embodiment has explained the case in which the information processing apparatus 100 includes the surface position detection unit 103. However, the present invention is not limited to this. For example, an apparatus having a function similar to the surface position detection unit 103 may be arranged independently of the information processing apparatus 100, and the information processing apparatus 100 may acquire the surface position detected by that apparatus.

13. Modification 10 of this Embodiment

The aforementioned embodiment has explained the case in which a coordinate transformation candidate group is generated by giving several types of small changes to estimated values of the coordinate transformation parameters, and a candidate which yields a maximum similarity is selected from the candidate group and is updated. However, the present invention is not limited to this.

For example, the influences of the six parameters in the estimated values of the coordinate transformation parameters on a similarity may be measured, and the coordinate transformation parameters may be updated to increase a similarity based on the measurement results.

In this case, if the estimated values of the coordinate transformation parameters at the current timing are expressed by:

$$p = (p_1, p_2, p_3, p_4, p_5, p_6)^T \qquad \text{[Mathematical 16]}$$

the coordinate transformation candidate group given with small changes of these estimated values in step S305 can be generated using, for example:

$$p_{1+} = (p_1 + d_1, p_2, p_3, p_4, p_5, p_6)^T \qquad \text{[Mathematical 17]}$$
$$p_{1-} = (p_1 - d_1, p_2, p_3, p_4, p_5, p_6)^T$$
$$\vdots$$
$$p_{6+} = (p_1, p_2, p_3, p_4, p_5, p_6 + d_1)^T$$
$$p_{6-} = (p_1, p_2, p_3, p_4, p_5, p_6 - d_1)^T$$

Then, the coordinate transformation is executed using this group of coordinate transformation candidates $P_{1+}, P_{1-}, \ldots, P_{6-}$ in step S306, and similarities for the respective candidates are calculated in step S307, as described in the above embodiment.

In this modification, in step S307 the influences of the parameters on the similarities are further calculated based on the similarities of the respective candidates like:

$$g_1 = (C_{p1+} - C_{p1-})^T \qquad \text{[Mathematical 18]}$$
$$g_2 = (C_{p2+} - C_{p2-})^T$$
$$\vdots$$
$$g_6 = (C_{p6+} - C_{p6-})^T$$

where $C_{p1+}, C_{p1-}, C_{p2+}, \ldots, C_{p6-}$ are the values of the similarities associated with the coordinate transformation candidates expressed by suffices calculated in step S307.

In step S308, in addition to selection of a candidate which yields a maximum similarity, as described in the above embodiment, estimated values p of the coordinate transformation at the current timing are updated to p', as given by:

$$p' = p + \alpha(g_1, g_2, g_3, g_4, g_5, g_6)^T \qquad \text{[Mathematical 19]}$$

where $\alpha$ is a scalar constant value which decides the magnitude of updating.

According to this method, the coordinate conversion parameters with a higher similarity can be estimated by a smaller number of times of repetition.

Note that in order to obtain the same effect, a downhill simplex method, Powell method, and the like may be used. Even when these methods are used, the coordinate transformation candidates can be generated and updated based on the similarity calculation results and the like in the same manner as in the above description.

Second Embodiment

In the first embodiment, an ultrasonic image and medical image are registered based on pieces of image information in these images. However, the present invention is not limited to this. Coordinate transformation parameters may be calculated using measurement results obtained by measuring the position and orientation of an ultrasonic probe in addition to the image information. This embodiment will be described in detail below.

<1. Functional Arrangement of Information Processing Apparatus>

Figure 11:
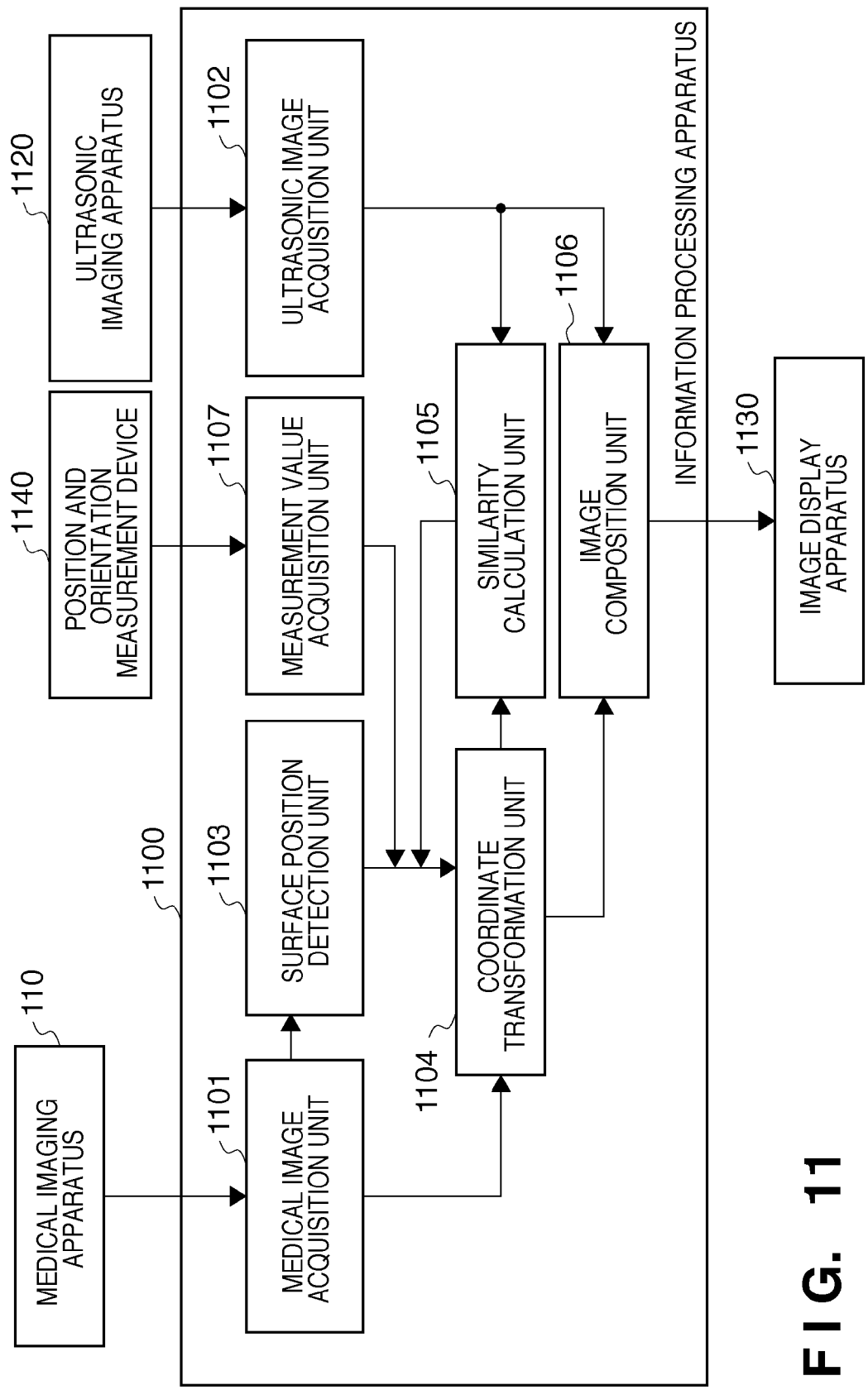
FIG. 11 is a block diagram showing the functional arrangement of an information processing apparatus 1100 according to the second embodiment.

FIG. 11 is a block diagram showing the functional arrangement of an information processing apparatus 1100 according to this embodiment. The information processing apparatus 1100 is connected to a medical imaging apparatus 1110, ultrasonic imaging apparatus 1120, and position and orientation measurement device 1140.

The medical imaging apparatus 1110 is an apparatus such as an X-ray CT or MRI, which captures a medical image of the interior portion of an examinee. The ultrasonic imaging apparatus 1120 is an apparatus which captures an image of a second region of the interior portion of the examinee via ultrasonic waves by bringing an ultrasonic probe (not shown) into contact with the examinee. The position and orientation measurement device 1140 (a third acquisition unit) is attached to the ultrasonic probe (not shown) of the ultrasonic imaging apparatus 1120, and measures the position and orientation of the ultrasonic probe.

A medical image acquisition unit 1101 acquires a medical image (first image) of the examinee captured by the medical imaging apparatus 1110. A surface position detection unit 1103 detects a surface position of the examinee by processing the first image, and generates that position information using position coordinates on a first coordinate system.

A coordinate transformation unit 1104 generates a second image obtained by coordinate-transforming the first image onto a second coordinate system based on the position information generated by the surface position detection unit 1103 and an output value of a similarity calculation unit 1105 (to be described later).

An ultrasonic image acquisition unit 1102 acquires an ultrasonic image (third image) captured by the ultrasonic imaging apparatus 1120. The similarity calculation unit 1105 calculates a similarity between the second and third images.

An image composition unit 1106 acquires the second and third images, and generates a composite image by compositing these images. An image display apparatus 1130 displays the composite image acquired from the image composition unit 1106 of the information processing apparatus 1100.

<2. Hardware Arrangement of Information Processing Apparatus>

Figure 12:
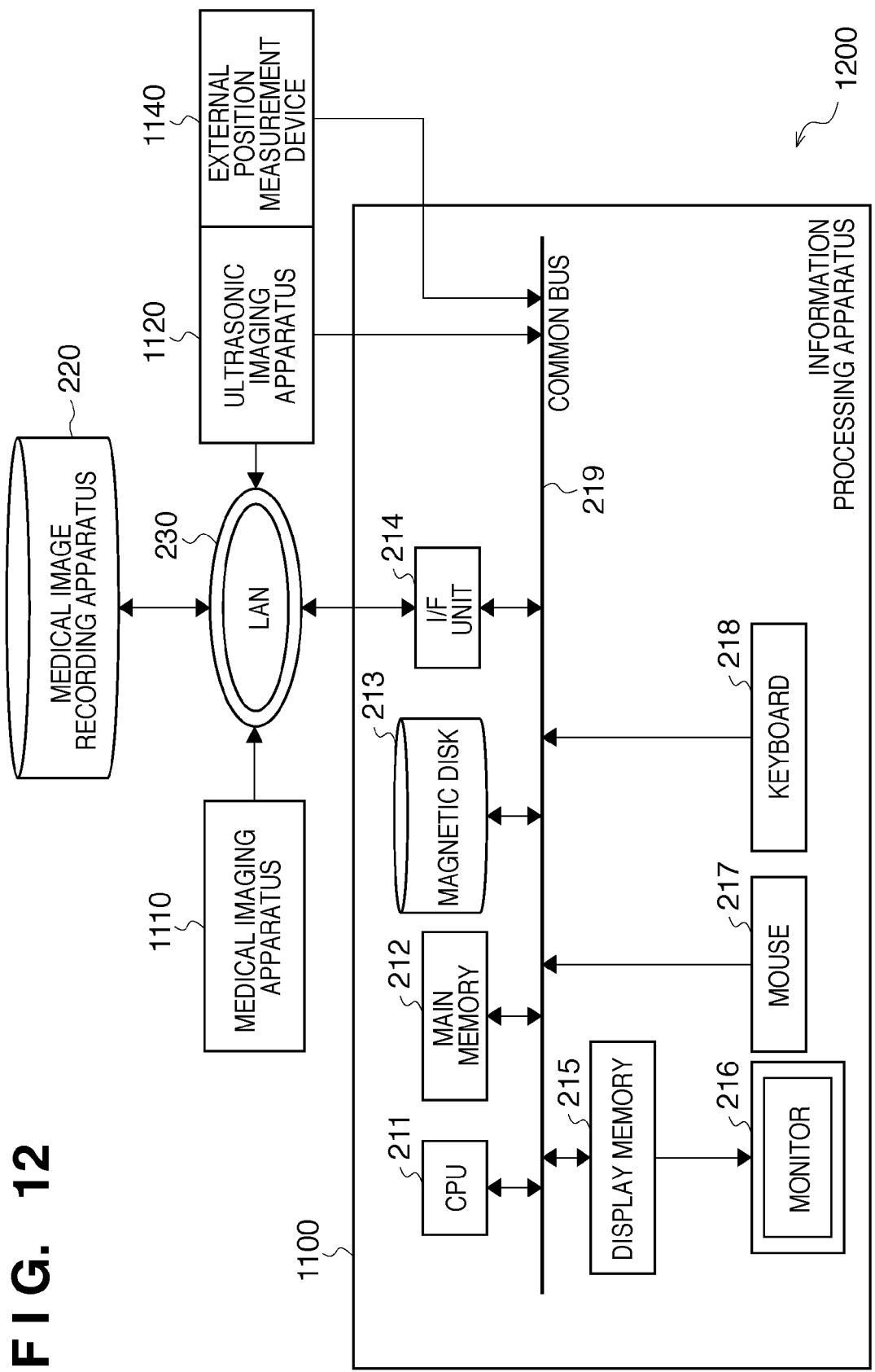
FIG. 12 is a block diagram showing the hardware arrangement of the information processing apparatus 1100 according to the second embodiment, and the network arrangement of an information processing system 1200 including the information processing apparatus.

FIG. 12 is a block diagram showing the hardware arrangement of the information processing apparatus 1100 according to this embodiment and the network arrangement of an information processing system 1200 including the information processing apparatus. As shown in FIG. 12, the information processing system 1200 has nearly the same network arrangement shown in FIG. 2 described in the first embodiment, except that the position and orientation measurement device 1140 is added.

The position and orientation measurement device 1140 is attached to the ultrasonic probe (not shown) of the ultrasonic imaging apparatus 1120, and measures the position and orientation of the ultrasonic probe. The position and orientation measurement device 1140 includes, for example, FASTRAK available from Polhemus, U.S.A. However, the position and orientation measurement device 1140 may have any other configurations as long as it can measure the position and orientation.

The position and orientation measurement device 1140 is further connected to a common bus 219 of the information processing apparatus 1100, and the information processing apparatus 1100 can acquire the position and orientation measurement result of the ultrasonic probe.

In this way, a difference of the information processing apparatus 1100 according to this embodiment from the first embodiment lies in that it acquires the measurement result from the position and orientation measurement device which measures the position and orientation of the ultrasonic probe. According to this embodiment, since an initial value of registration is set and a deformation of an examinee is corrected using the measurement result obtained by measuring the position and orientation of the ultrasonic probe, more advanced registration can be attained.

<3. Details of Ultrasonic Probe and Position and Orientation Measurement Device>

Figure 13:
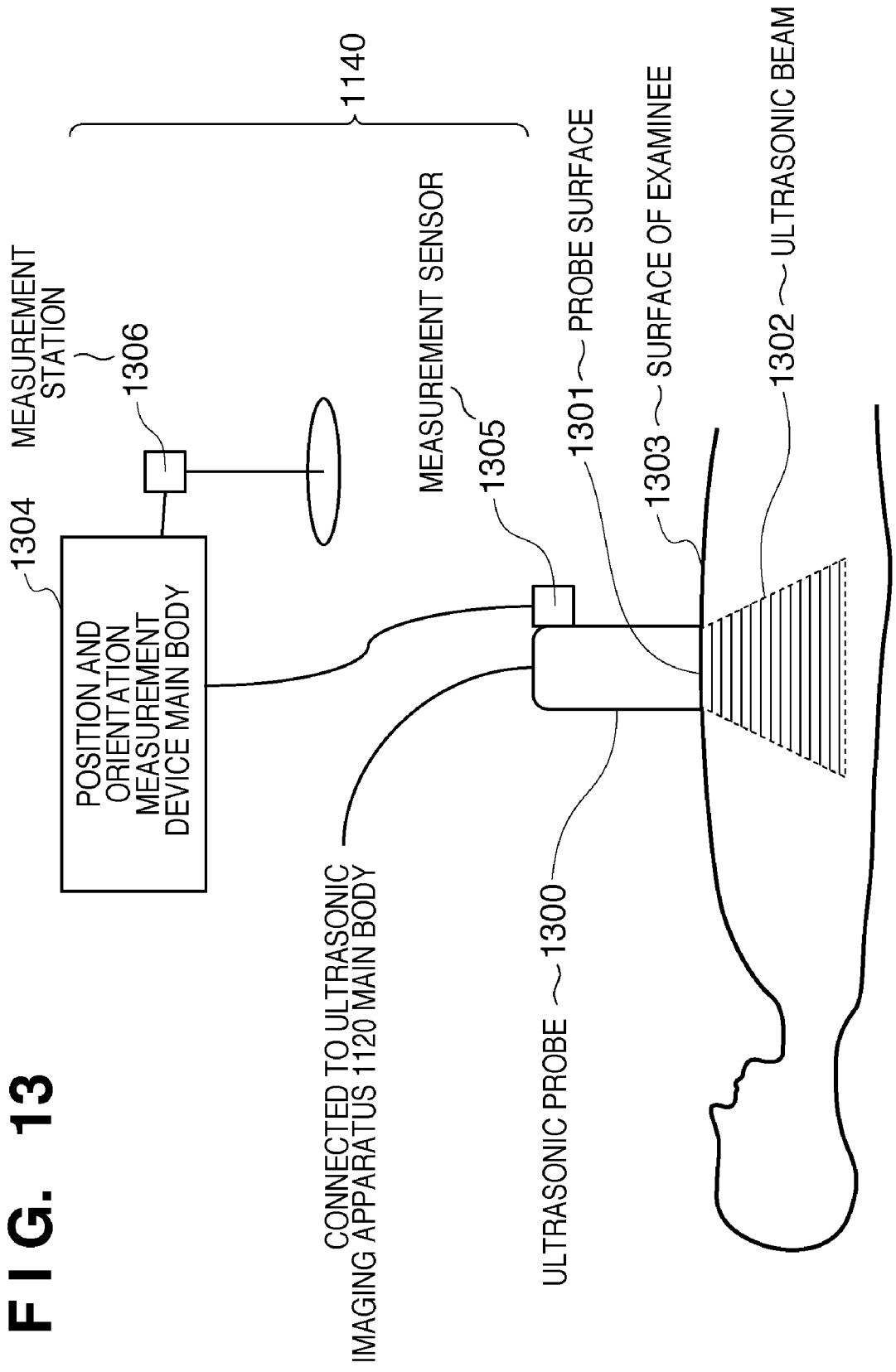
FIG. 13 is a view showing details of an ultrasonic probe which configures an ultrasonic imaging apparatus 1120, and a position and orientation measuring device 1140.

FIG. 13 is a view showing details of the ultrasonic probe which configures the ultrasonic imaging apparatus 1120, and the position and orientation measurement device 1140. As shown in FIG. 13, a probe surface 1301 of an ultrasonic probe 1300 is brought into contact with a surface 1303 of an examinee when the probe 1300 is used.

The probe surface 1301 emits an ultrasonic beam 1302 to the examinee, and the ultrasonic probe 1300 receives an acoustic signal obtained when ultrasonic waves are reflected by the interior portion of the examinee, thereby acquiring an ultrasonic image of the interior portion of the examinee.

Reference numeral 1304 denotes a position and orientation measurement device main body, which configures the position and orientation measurement device 1140, and includes a position and orientation measurement sensor 1305 and position and orientation measurement station 1306.

The position and orientation measurement station 1306 is fixed in position in a measurement space. Assume that the position and orientation measurement sensor 1305 is fixedly attached to the ultrasonic probe 1300, and moves interlockingly with the movement of the ultrasonic probe 1300 by, for example, the user.

The position and orientation measurement device main body 1304 exchanges data between the position and orientation measurement station 1306 and position and orientation measurement sensor 1305, and measures a relative position and orientation of the position and orientation measurement sensor 1305 with reference to the position and orientation measurement station 1306.

When a magnetic sensor is used as the position and orientation measurement device 1140, the position and orientation measurement station 1306 includes a magnetic field generator (transmitter) which generates a magnetism. The position and orientation measurement sensor 1305 includes a magnetic sensor which measures the strength of the magnetism. When the magnetism generated by the position and orientation measurement station 1306 is measured by the position and orientation measurement sensor 1305, the relative position and orientation between them can be measured. Note that the aforementioned method can obtain the same function even when the arrangements of the magnetic field generator and magnetic sensor are exchanged.

The position and orientation measurement device 1140 may include an optical sensor. For example, a rigid body configured by a plurality of markers each including an emission or reflection member of, for example, infrared rays, may be attached to the ultrasonic probe 1300, and an imaging device such as a camera set in the measurement space may capture an image of this rigid body, thereby measuring the position and orientation of the rigid body. Alternatively, an imaging device may be fixedly attached to the ultrasonic probe 1300 to capture an image of markers set in the space, thereby measuring the position and orientation of the imaging device. Note that the position and orientation measurement device 1140 shown in FIG. 11 in this embodiment may adopt arbitrary measurement methods in place of the aforementioned non-contact measurement method.

The present invention relates to registration between a medical image (first image) captured on a first coordinate system and an ultrasonic image (third image) captured on a third coordinate system.

<4. Description about Positional Relationship between First Coordinate System and Third Coordinate System>

Figure 14:
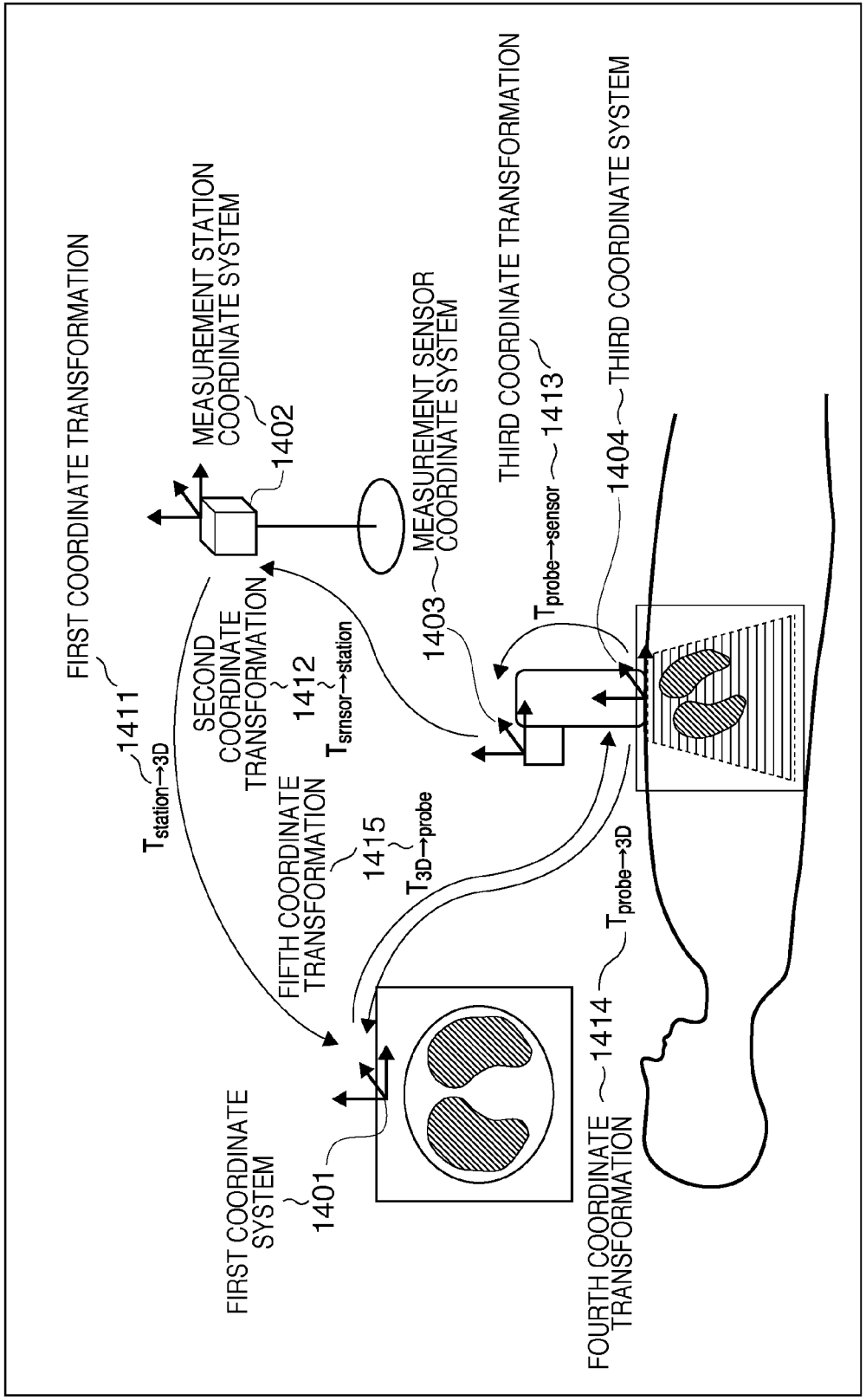
FIG. 14 is a view for explaining the relationship among first and third coordinate systems, and other coordinate systems associated with registration processing.

FIG. 14 is a view for explaining the relationship among the first and third coordinate systems, and other coordinate systems associated with the registration processing. Referring to FIG. 14, a first coordinate system 1401 is a coordinate system which serves as a reference of a medical image (first image). A measurement station coordinate system 1402 is a coordinate system which is defined with reference to the position and orientation measurement station 1306 shown in FIG. 13 on an actual space where the ultrasonic imaging apparatus 1120 performs imaging.

Assume that the measurement station coordinate system 1402 in this embodiment is a coordinate system fixed on a physical space. A measurement sensor coordinate system 1403 is a coordinate system which is defined with reference to the position and orientation measurement sensor 1305 shown in FIG. 13. In this embodiment, as described above using FIG. 13, the position and orientation measurement sensor 1305 is fixedly attached to the ultrasonic probe 1300. Therefore, the measurement sensor coordinate system 1403 is a coordinate system whose reference moves on the physical space upon movement/rotation of the ultrasonic probe by, for example, user operations. A third coordinate system 1404 is a reference coordinate system on an ultrasonic image (third image) which has, as an origin, a position corresponding to the probe surface 1301 shown in FIG. 13.

A first coordinate transformation 1411 is that from the measurement station coordinate system 1402 to the first coordinate system 1401. This coordinate transformation is that which expresses the relationship between the position and orientation of the examinee on the measurement station coordinates, and the position of a captured image of the examinee on the first image. This coordinate transformation may be provisionally determined by, for example, a user's input operation.

A second coordinate transformation 1412 is that from the measurement sensor coordinate system 1403 to the measurement station coordinate system 1402. This coordinate transformation expresses the position and orientation measured by the position and orientation measurement device 1140 in FIG. 11, and is calculated based on the position and orientation measurement values acquired by the position and orientation measurement device 1140. Therefore, in the description of this embodiment, these values are used intact.

A third coordinate transformation 1413 is that from the third coordinate system 1404 to the measurement sensor coordinate system 1403. This coordinate transformation relates to the probe surface 1301, the emission direction of the ultrasonic beam 1302, and the position and orientation measurement sensor 1305 in FIG. 13, and is determined based on the relationship between image coordinates in the ultrasonic image (third image) and the measurement sensor coordinate system 1403.

This coordinate transformation can also be determined using the measurement result of the position and orientation measurement device when the probe surface 1301 in FIG. 13 is brought into contact with the surface of an object with a given shape. Alternatively, the coordinate transformation may be determined based on a result obtained by physically and directly measuring the position and orientation relationship between the position and orientation measurement sensor 1305 and probe surface 1301.

A fourth coordinate transformation 1414 is that from the third coordinate system 1404 to the first coordinate system 1401. This coordinate transformation can be expressed as a combination of the above coordinate transformations like:

$$T_{probe \to 3D} = T_{station \to 3D} T_{srnsor \to station} T_{probe \to sensor}$$ [Mathematical 20]

A fifth coordinate transformation 1415 is that from the first coordinate system 1401 to the third coordinate system 1404. This coordinate transformation is an inverse transformation of the coordinate transformation 1414, and can be expressed by:

$$\begin{aligned} T_{3D \to probe} &= T_{probe \to 3D}^{-1} \\ &= T_{probe \to sensor}^{-1} T_{srnsor \to station}^{-1} T_{station \to 3D}^{-1} \end{aligned}$$ [Mathematical 21]

Of the aforementioned coordinate transformations, the first coordinate transformation 1411 is provisionally determined by, for example, a user's input operation. However, in practice, errors may often be generated due to a probe pressure or the body movement of the examinee himself or herself in the ultrasonic imaging apparatus 1120.

In the above description, the second coordinate transformation 1412 is determined based on the measurement value of the position and orientation measurement device. However, in practice, this measurement value may often be mixed with measurement errors.

In the above description, the third coordinate transformation 1413 is set by executing calibration beforehand. However, in practice, this calibration result may often include errors. During imaging by the ultrasonic imaging apparatus, the position and orientation relationship between the measurement sensor and ultrasonic probe may have changed to often cause errors.

Therefore, the fifth coordinate transformation 1415 obtained by combining these coordinate transformations may often include errors. In this embodiment, by correcting the fifth coordinate transformation 1415 by registration processing to be described later, a true coordinate transformation from the first coordinate system to the third coordinate system is estimated.

<5. Sequence of Registration Processing>

Figure 15:
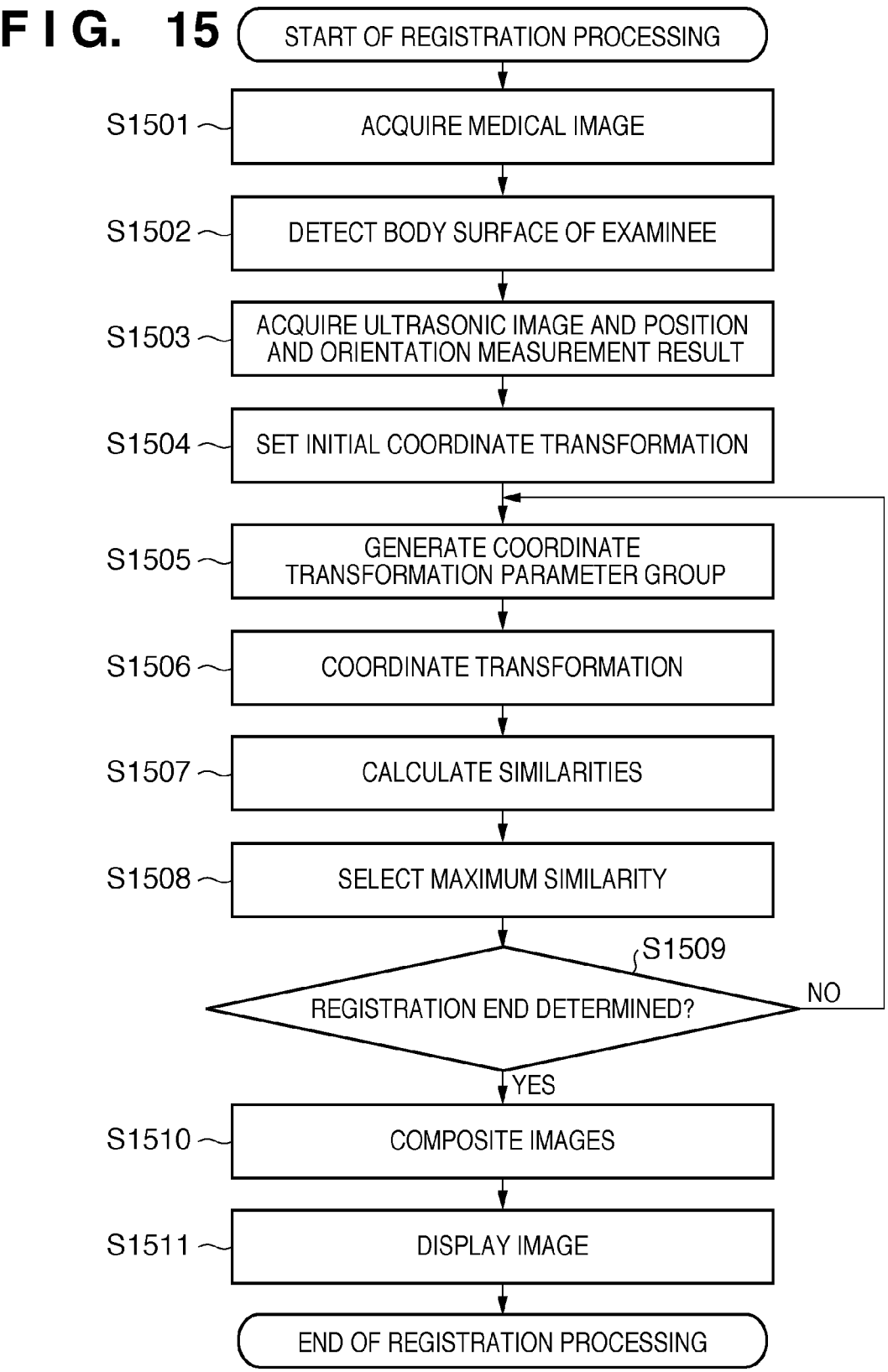
FIG. 15 is a flowchart showing the sequence of registration processing in the information processing apparatus 1100.

FIG. 15 is a flowchart showing the sequence of the registration processing in the information processing apparatus 1100 according to this embodiment. Steps S1501 to S1510 in FIG. 15 include many processing steps having the same processing contents as in steps S301 to S310 in the first embodiment described above using FIG. 3. For this reason, only steps that execute processes different from the first embodiment will be described below.

<5.1 Step S1503 (Ultrasonic Image/Position and Orientation Measurement Result Acquisition Processing)>

In step S1503, a measurement value acquisition unit 1107 in FIG. 11 acquires the coordinate transformation 1412 shown in FIG. 14. Since provisional values are set in advance in the first coordinate transformation 1411 and third coordinate transformation 1413, the fifth coordinate transformation 1415 can be provisionally calculated using them from (Mathematical 21). The following description will be given under the assumption that a value $T_{3D \to probe}$ in (Mathematical 21) is directly obtained from the measurement value acquisition unit 1107 in FIG. 11.

In step S1503, the aforementioned processing is executed, and the ultrasonic image acquisition unit 1102 acquires an ultrasonic image of the examinee captured by the ultrasonic imaging apparatus 1120. Since this processing is the same as that in step S303 in the first embodiment, a description thereof will not be repeated.

<5.2 Step S1504 (Initial Coordinate Transformation Setting Processing)>

In step S1504, the coordinate transformation unit 1104 in FIG. 11 sets an initial coordinate transformation $T_{init}$ from the first coordinate system to the second coordinate system as in the first embodiment. In this embodiment, processing for making this second coordinate system close to (or be matched with) the third coordinate system, that is, registration processing is executed. The initial coordinate transformation setting method will be described below using FIG. 16.

Figure 16:
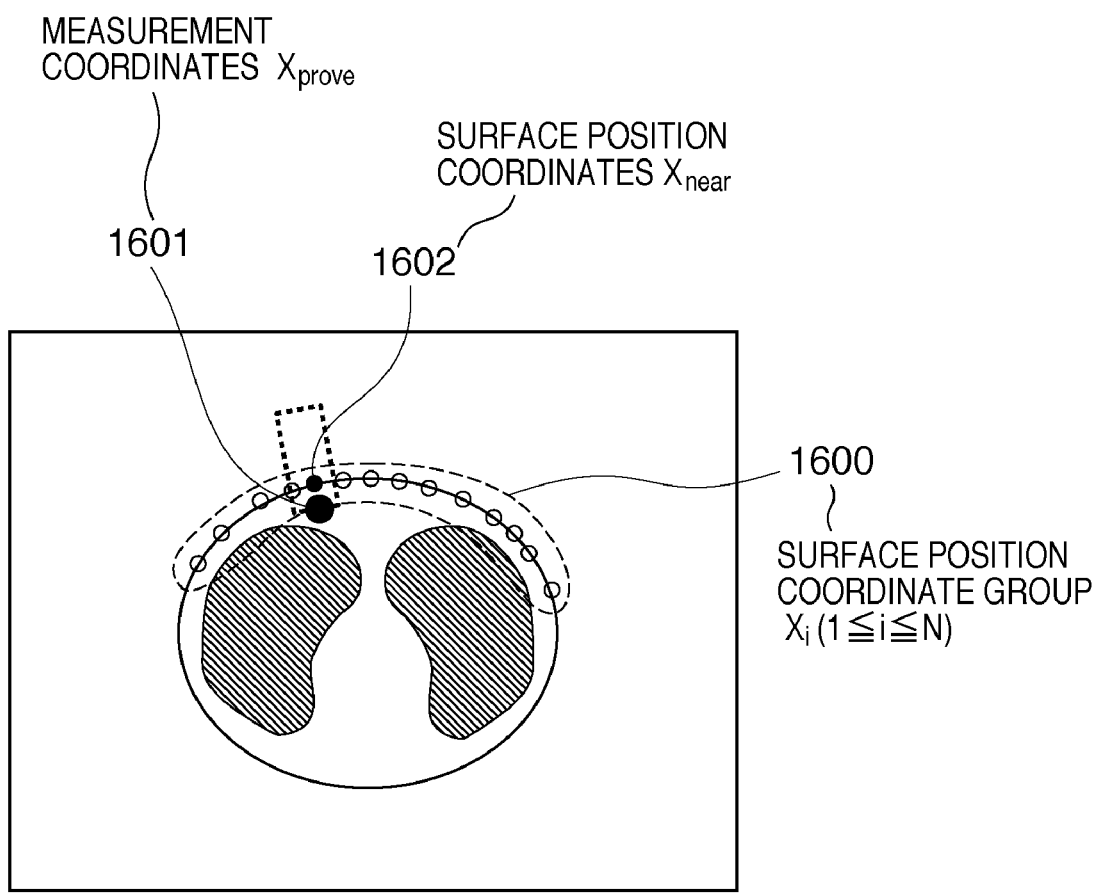
FIG. 16 is a view for explaining initial coordinate transformation setting processing.

Referring to FIG. 16, a surface position coordinate group 1600 is a coordinate group of surface positions of the examinee on the first coordinate system detected in step S1502, and is described by $x_{si} = (x_{si}, y_{si}, z_{si})^T$ for $1 \leq i \leq N$.

Measurement coordinates 1601 are position coordinates of a point where the ultrasonic probe is in contact with the examinee, which coordinates are acquired in step S1503, and are described by $x_{probe} = (x_{probe}, y_{probe}, z_{probe})^T$. Assume that $x_{probe}$ is obtained by coordinate-transforming an origin of the third coordinate system onto the first coordinate system using (Mathematical 20).

In this embodiment, the initial coordinate transformation $T_{init}$ can be set in, for example, the following sequence.

Surface position coordinates 1602 closest to the measurement coordinates 1601 of the probe surface are selected from the surface position coordinate group 1600 of the examinee on the first coordinate system.

This selection can be attained by calculating distances of all the position coordinates in the surface position coordinate group 1600 to the measurement coordinates 1601 to obtain position coordinates with the smallest distance. Note that the selected surface position coordinates 1602 are described by $x_{near} = (x_{near}, y_{near}, z_{near})^T$.

Assuming that an infinite number of coordinate positions in the surface position coordinate group 1600 are detected at infinitesimal intervals in an ideal state free from any body movement of the examinee and any deformation of the surface shape at the times of capturing the medical image and ultrasonic image, $x_{probe}$ and $x_{near}$ assume identical values.

However, in practice, $x_{probe}$ and $x_{near}$ often assume different values due to various factors. A positional deviation between the measurement coordinates 1601 and surface position coordinates 1602 in FIG. 16 indicates it. In this embodiment, the coordinate transformation 1411 is corrected using a vector $v = x_{near} - x_{probe}$ of this deviation amount like:

$$T'_{station \to 3D} = \begin{pmatrix} I & v \\ 0 & 1 \end{pmatrix} T_{station \to 3D} \qquad \text{[Mathematical 22]}$$

Then, the coordinate transformation combined using it is calculated by:

$$T_{3D \to probe}' = T_{probe \to sensor}^{-1} T_{sensor \to station}'^{-1} T_{station \to 3D'}^{-1} \qquad \text{[Mathematical 23]}$$

The calculated coordinate transformation is set as the initial coordinate transformation $T_{init}$.

According to the aforementioned method, an effect of setting the coordinate transformation in which translation component errors included in the coordinate transformation $T_{3D \to probe}$ as the initial value is provided.

The initial coordinate transformation setting method is not limited to this. For example, a method of calculating the surface shape of the examinee, and then setting the initial coordinate transformation based on the relationship between this shape and ultrasonic wave emission direction is also available.

In this case, a method of setting the initial coordinate transformation by generating the surface shape of the examinee using, for example, polygon patches from the surface position coordinate group 1600, and executing matching between normal directions to these polygon patches and an orientation component of the position and orientation measurement value may be used.

This matching is executed under the assumption that, for example, the ultrasonic wave emission direction matches the normal direction to the surface of the examinee in practice. Then, an inner product of the normal direction to each polygon patch and the ultrasonic wave emission direction, which is calculated from a rotation component of the position and orientation measurement value, is calculated.

Then, a polygon patch with the largest inner product value is selected, and a rotation component of the initial coordinate transformation $T_{init}$ is set so that the normal direction to this polygon patch matches the ultrasonic wave emission direction. In this case, an effect of setting a coordinate transformation in which rotation component errors included in the coordinate transformation $T_{3D \to probe}$ are corrected as an initial value can be provided.

A method obtained by combining the aforementioned methods forms one embodiment of the present invention. For example, distances between the measurement coordinates 1601 and positions in the surface position coordinate group 1600 of the examinee in FIG. 16 are calculated. Then, inner products between the normal directions to the surface shape around the respective positions of the surface position coordinate group 1600 and the ultrasonic wave emission direction are calculated. Then, surface position coordinates $x_{near}$ are selected based on an evaluation which combines them like:

$$x_{near} = \underset{x_i}{\operatorname{argmax}} \{ -\|x_i - x_{probe}\| + \lambda v_i \cdot v_{probe} \} \qquad \text{[Mathematical 24]}$$

After that, the initial coordinate transformation $T_{init}$ can be set based on the selected surface position coordinates $x_{near}$ and the normal direction of the surface shape around the coordinates.

Note that $v_i$ is a unit vector of the normal direction of the i-th surrounding polygon patch of the surface position coordinate group 1600, and $v_{probe}$ is a unit vector of the ultrasonic wave emission direction. According to this method, an effect of setting a more likely coordinate transformation in consideration of both the surface position and surface shape of the examinee as an initial value can be provided.

As can be seen from the above description, this embodiment is characterized in that errors of the position measurement result are corrected while using the constraint condition that the imaging reference point of the ultrasonic probe is in contact with the body surface of the examinee on the physical space.

As a result, with the information processing apparatus 1100 according to this embodiment, the medical image and ultrasonic image can be registered at high speed while correcting the influence of errors included in the position and orientation measurement value of the ultrasonic probe.

6. Modification 1 of this Embodiment

This embodiment has exemplified the case in which the relationship among the coordinate systems defined in FIG. 14, that is, the coordinate transformation is expressed by a rigid transformation. However, the present invention is not limited to this. For example, when the position and orientation measurement value acquired in step S1503 is obtained precisely with respect to the physical space, a positional deviation between the surface position coordinates 1602 of the examinee and the measurement coordinates 1601 of the probe surface can be considered as a deformation due to the probe pressure. A case of registration in consideration of this deformation amount will be explained below.

This modification can be implemented by replacing the processes in steps S1504 to S1506 described in this embodiment by the following processes.

In step S1504, the measurement coordinates 1601 of the probe surface position and the nearest surface position coordinates 1602 of the examinee are associated with each other as in the process of this embodiment. Then, a deviation between these two coordinates undergoes deformation registration using, for example, an FFD (Free Form Deformation) method in place of the rigid transformation. Note that details of the FFD method are disclosed in, for example, the following reference (to be referred to as non-patent reference 2 hereinafter):

T. W Sederberg "Free-form deformation of solid geometric models" (Proc. SIGGRAPH '86, vol. 20, no. 4 pp. 151-160, 1986).

Figure 17A:
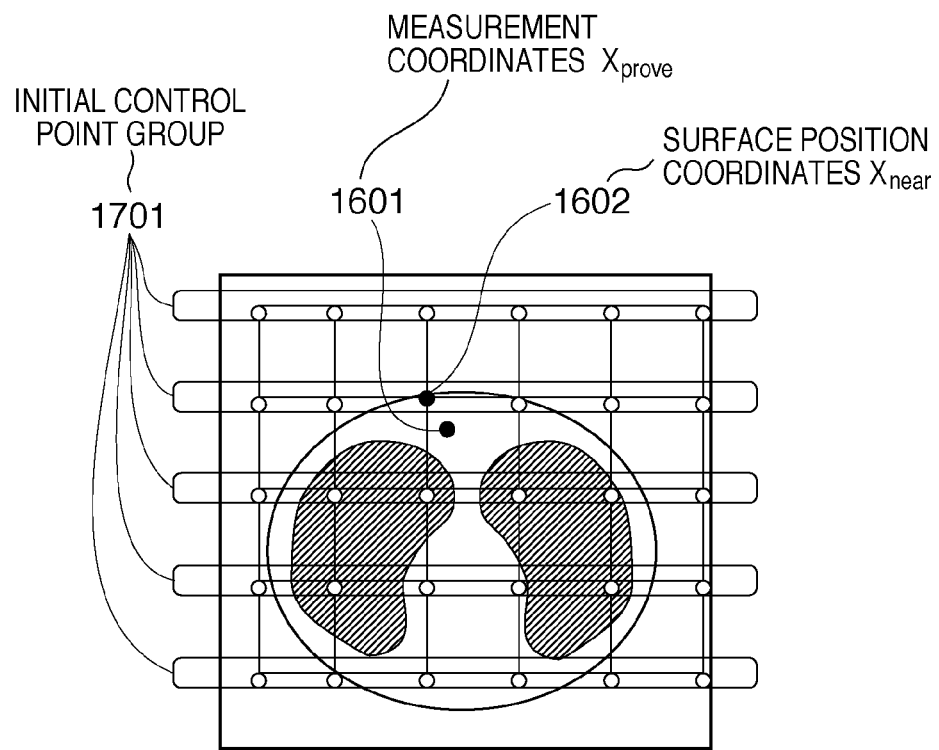
FIG. 17A is a view for explaining registration processing by the information processing apparatus 1100 according to a modification of the second embodiment.
Figure 17B:
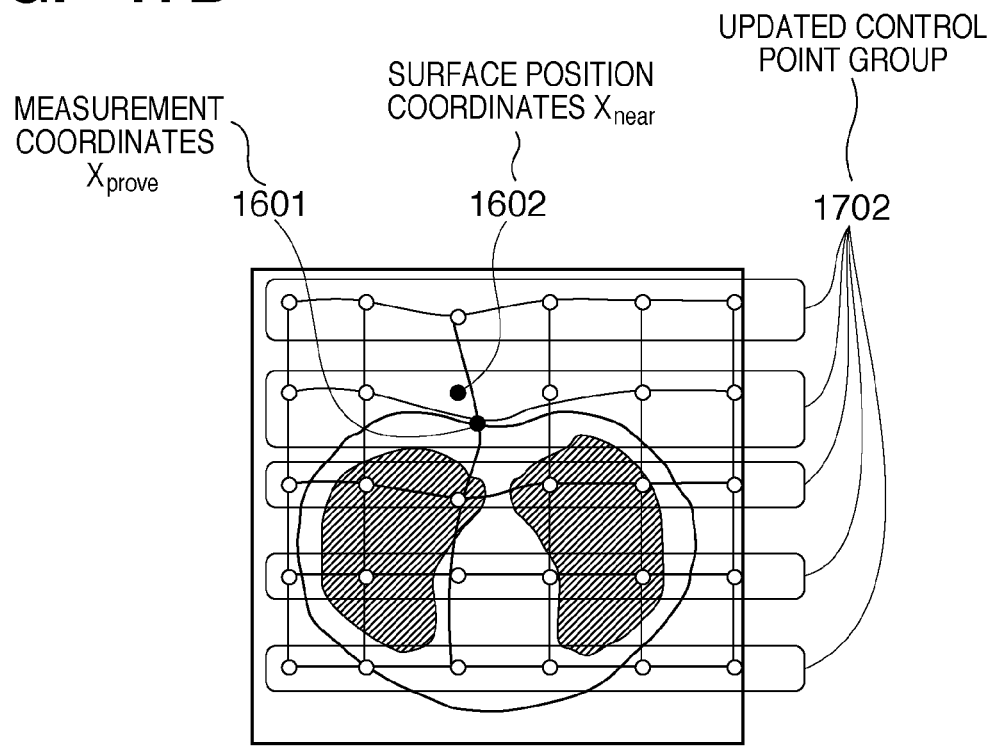
FIG. 17B is a view for explaining registration processing by the information processing apparatus 1100 according to a modification of the second embodiment.

For example, initial control point groups 1701 on meshes are laid out with reference to the surface position coordinates 1602 of the examinee on the first coordinate system, which are associated, as shown in FIG. 17A. Then, the control point groups are moved based on the measurement coordinates 1601 of the probe surface on the first coordinate system, thus obtaining updated control point groups 1702.

That is, in step S1504 of the second embodiment, rigid transformation parameters are set. However, in this modification, the moving amounts of the control point groups are set as coordinate transformation parameters.

In step S1505, a candidate group of a plurality of coordinate transformation parameters is generated by moving the respective control points by small amounts. This candidate group may be generated by moving all control points by small amounts or moving only control points around the surface position coordinates 1602 used as a reference upon laying out the control points.

In step S1506, the coordinate transformation unit 1104 executes a non-linear coordinate transformation based on the moving amounts of the control points. According to non-patent reference 2 above, this coordinate transformation can generate a second image on the second coordinate system by applying a non-linear transformation to the first image on the first coordinate system using B-Spline interpolation processing.

According to this method, an effect of allowing precise registration with respect to a spatially non-linear deformation of the examinee due to, for example, the probe pressure can be provided.

The coordinate transformation method including a non-linear deformation is not limited to the above method, and for example, a Thin-Plate Spline (TPS) method can be used. Note that the TPS method is disclosed in the following reference (to be referred to as non-patent reference 3 hereinafter):
Fred L. Bookstein "Principal Warps: Thin-Plate Splines and the Decomposition of Deformations" (IEEE Transaction on Patten Analysis and Machine Intelligence. Vol. 11, No. 6, 1989).

In addition to the above methods, the coordinate transformation from the first coordinate system to the second coordinate system can be calculated by estimating a deformation amount of the examinee using a finite element method (FEM: Finite Element Method). According to this method, an effect of estimating a deformation of the examinee due to the probe pressure with physically high precision can be provided.

The present invention is not limited to the aforementioned method, and each of embodiments using any other coordinate transformation methods can form one embodiment of the present invention.

Other Embodiments

The present invention can also be implemented by executing the following processing. That is, in this processing, software (program) which implements the functions of the aforementioned embodiments is supplied to a system or apparatus via a network or various storage media, and a computer (or CPU or MPU) of that system or apparatus reads out and executes the program.

The present invention is not limited to the above embodiments and various changes and modifications can be made without departing from the spirit and scope of the present invention. Therefore, to apprise the public of the scope of the present invention, the following claims are appended.

This application claims the benefit of Japanese Patent Application No. 2008-311560, filed Dec. 5, 2008, which is hereby incorporated by reference herein in its entirety.

The invention claimed is:

1. An information processing apparatus for registering a first image and a second image, wherein the first image is captured by a first imaging unit which captures an image of a state of an interior portion of an object under condition where a probe in the first imaging unit is situated at a non-contact position with respect to the object, and wherein the second image is captured by a second imaging unit which captures an image of a state of an interior portion of an object under condition where a probe in the second imaging unit is situated at a position in contact with a body surface of the object, comprising:
a first acquisition unit configured to acquire the first image;
a second acquisition unit configured to acquire the second image;
a detecting unit configured to detect a position of the body surface of the object based on the first image;
a third acquisition unit configured to acquire a position of a surface of the probe in the second imaging unit when the second imaging unit captures the second image; and
a coordinate transformation unit configured to calculate a deformation amount of the object, which is caused when the probe in the second imaging unit is brought into contact with the body surface of the object, based on the position of the body surface of the object which is detected by the detecting unit based on the first image and the position of the surface of the probe in the second imaging unit which is acquired by the third acquisition unit, and estimate a coordinate transformation parameter for transforming the coordinate between the first image and the second image based on the calculated deformation amount.

2. The information processing apparatus according to claim 1, wherein said coordinate transformation unit calculates the deformation amount of the object by estimating a pressure, which is generated when the probe in the second imaging unit is brought into contact with the body surface of the object, based on the position of the body surface of the object which is detected by the detecting unit based on the first image and the position of the surface of the probe in the second imaging unit which is acquired by the third acquisition unit.

3. An information processing apparatus for registering a first image and a second image, wherein the first image is captured by a first imaging unit which captures an image of a state of an interior portion of an object under a condition where a probe in the first imaging unit is situated at a non-contact position with respect to the object, and wherein the second image is captured by a second imaging unit which captures an image of a state of an interior portion of an object under condition where a probe in the second imaging unit is situated at a position in contact with a body surface of the object, the information processing apparatus comprising:
a first acquisition unit configured to acquire the first image;
a second acquisition unit configured to acquire the second image;
a detecting unit configured to detect a position of the body surface of the object based on the first image; and
a coordinate transformation unit configured to estimate a coordinate transformation parameter for transforming the coordinate between the first image and the second image, based on a similarity between the first image and the second image,
wherein the coordinate transformation parameter is estimated in accordance with a constraint condition derived by the position of the body surface of the object which is detected by the detecting unit based on the first image and the position of the surface of the probe in the second imaging unit when the second imaging unit captures the second image.

4. The information processing apparatus according to claim 3, wherein said coordinate transformation unit estimates the coordinate transformation parameter by searching a range limited to coordinate transformation parameters which satisfy the constraint condition.

5. The information processing apparatus according to claim 3, wherein said coordinate transformation unit deals with the constraint condition as a penalty when said coordinate transformation unit evaluates the estimated coordinate transformation parameter.

* * * * *